(12) United States Patent
Greene et al.

(10) Patent No.: US 11,312,784 B2
(45) Date of Patent: Apr. 26, 2022

(54) IGG BINDING PEPTIDES AND MULTIFUNCTIONAL ANTIGEN-BINDING PROTEINS COMPRISING THE SAME

(71) Applicant: THE TRUSTEES OF THE UNIVERSITY OF PENNSYLVANIA, Philadelphia, PA (US)

(72) Inventors: Mark I. Greene, Penn Valley, PA (US); Hongtao Zhang, Paoli, PA (US); Zhiqiang Zhu, Philadelphia, PA (US); Lian Lam, Philadelphia, PA (US); Zheng Cai, Wynnewood, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 281 days.

(21) Appl. No.: 16/309,969

(22) PCT Filed: Jun. 16, 2017

(86) PCT No.: PCT/US2017/037881
§ 371 (c)(1),
(2) Date: Dec. 14, 2018

(87) PCT Pub. No.: WO2017/218897
PCT Pub. Date: Dec. 21, 2017

(65) Prior Publication Data
US 2020/0216555 A1    Jul. 9, 2020

Related U.S. Application Data

(60) Provisional application No. 62/351,335, filed on Jun. 17, 2016.

(51) Int. Cl.
| | |
|---|---|
| *C07K 14/195* | (2006.01) |
| *C07K 19/00* | (2006.01) |
| *A61K 38/00* | (2006.01) |
| *C07K 16/28* | (2006.01) |
| *A61P 35/00* | (2006.01) |
| *C07K 14/555* | (2006.01) |

(52) U.S. Cl.
CPC .......... *C07K 16/2896* (2013.01); *A61P 35/00* (2018.01); *C07K 14/195* (2013.01); *C07K 14/555* (2013.01); *C07K 19/00* (2013.01); *A61K 38/00* (2013.01); *C07K 2317/622* (2013.01); *C07K 2319/21* (2013.01); *C07K 2319/30* (2013.01); *C07K 2319/74* (2013.01)

(58) Field of Classification Search
CPC combination set(s) only.
See application file for complete search history.

(56) References Cited

U.S. PATENT DOCUMENTS

| | | | |
|---|---|---|---|
| 2012/0135936 A1 | 5/2012 | Cervenakova | |
| 2012/0164066 A1* | 6/2012 | Greene | A61K 38/16 424/1.49 |
| 2014/0234221 A1* | 8/2014 | Greene | A61P 35/00 424/9.1 |

FOREIGN PATENT DOCUMENTS

| | | | |
|---|---|---|---|
| WO | WO2015/021444 | * | 2/2015 |
| WO | 2015041303 | | 3/2015 |

OTHER PUBLICATIONS

Muguruma et al (Bioconjugate Chemistry, Jun. 15, 2016, 27:1606-1613).*
Sockolosky et al. (PLoS One, 2014, 9:e102566, internet pp. 1-10).*
Kang et al (Macromolecular Research, 2015, 23:876-881).*
Cai et al (Cancer Research, 2013, 73:2619-2627)(IDS).*
Cai et al., 2013, scFv-8ased "Grababody" as a General Strategy to Improve Recruitment of Immune Effector Cells to Antibody-Targeted Tumors, Cancer Res.,73:2619-2627.
Graille et al., 2000, Crystal structure of a *Staphylococcus aureus* protein A domain complexed with the Fab fragment of a human IgM antibody: structural basis for recognition of B-cell receptors and superantigen activity, Proc Natl Acad Sci USA, 97:5399-5404.
Holm et al., 2010, Dali server: conservation mapping in 3D, Nucleic acids research, 38(Web Server issue):W545-549.
International Search Report for PCT/US17/37881 (4 pages).
Schwede et al., 2003, Swiss-Model: An automated protein homology-modeling server, Nucleic Acids Research, 31:3381-3385.
Written Opinion for PCT/US17/37881 (4 pages).
Zhang, 2013, Empowering scFv with effector cell functions for improved anticancer therapeutics, Oncoimmunology, 2:e24439 (3 pages).

* cited by examiner

*Primary Examiner* — Laura B Goddard
(74) *Attorney, Agent, or Firm* — Riverside Law LLP

(57) ABSTRACT

Disclosed herein are multifunctional antigen-binding proteins comprising at least one multifunctional recombinant protein scaffold and at least one antigen-specific binding domain. Polynucleotides encoding the multifunctional antigen-binding proteins, vectors containing the disclosed polynucleotides, and cells that have been genetically engineered to express the polynucleotide are also provided. Methods of using the multifunctional antigen-binding proteins are disclosed.

19 Claims, 5 Drawing Sheets
Specification includes a Sequence Listing.

T6-17

Control (anti-mouse, FITC)

4D5scFvZZ

4D5scFv-huZZ (2FCW)

4D5scFv-1V66

4D5scFv-huZZ

4D5scFv-2FCW (WT)

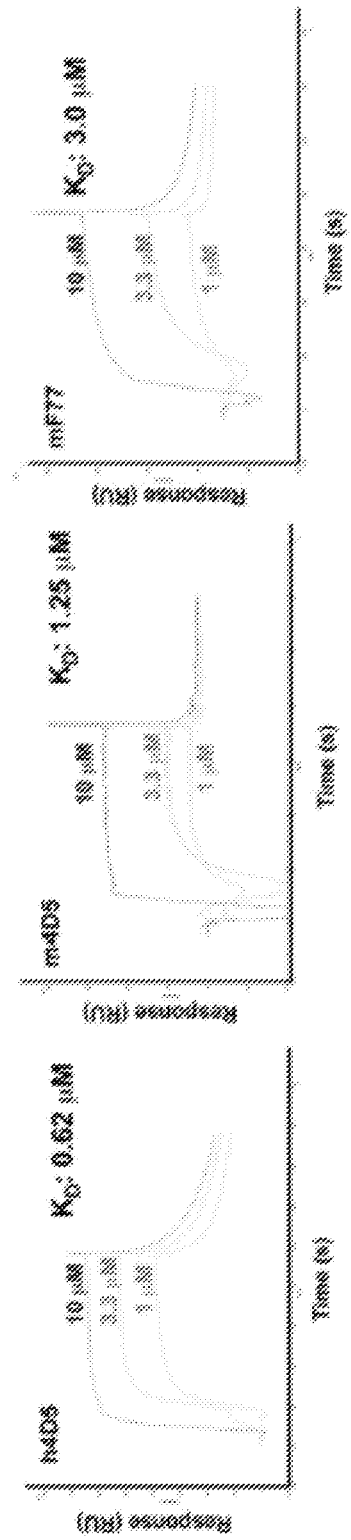
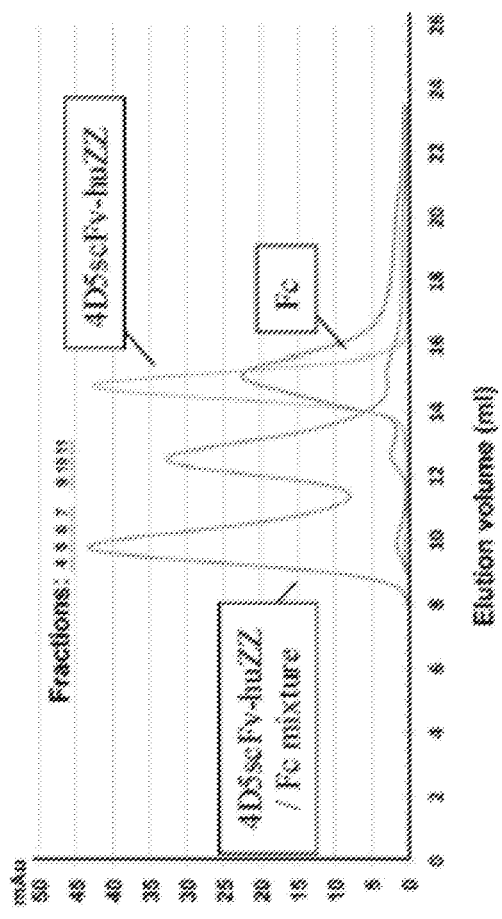
FIG. 4A
FIG. 4B
FIG. 4C

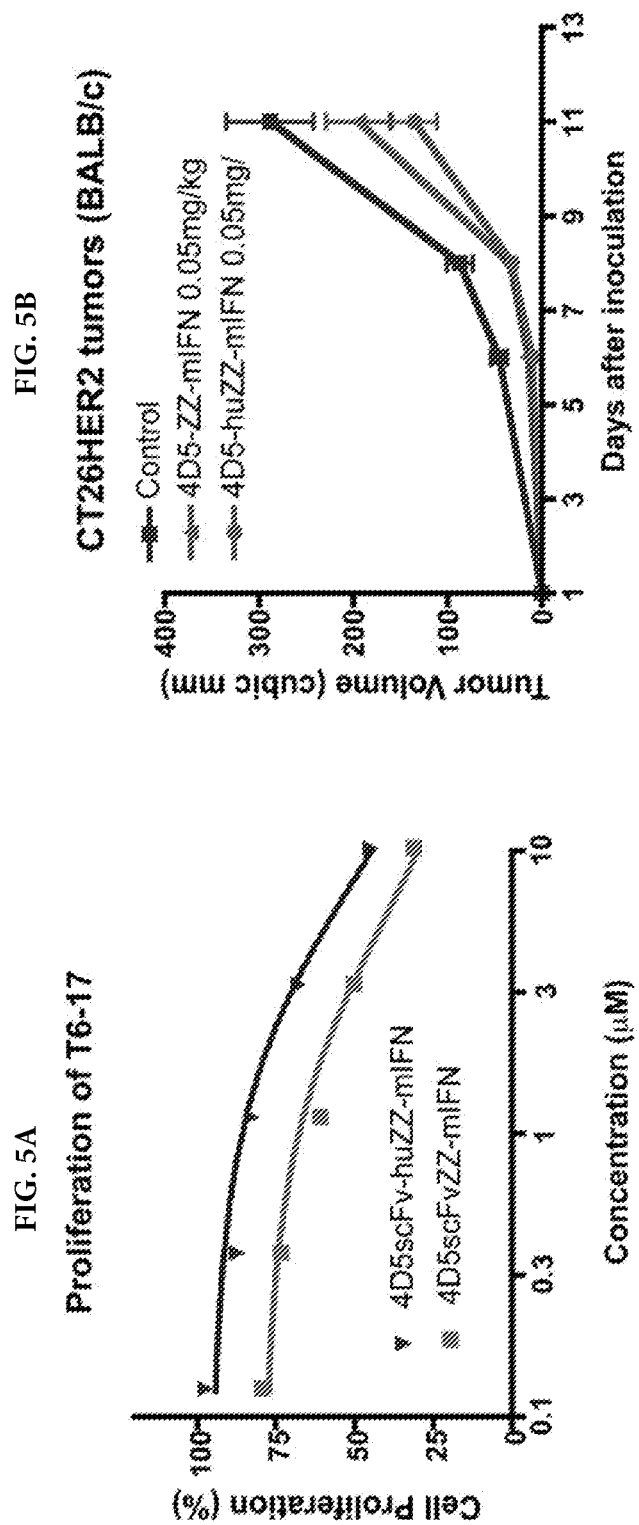

SEQUENCE LISTING

<160> NUMBER OF SEQ ID NOS: 38

<210> SEQ ID NO 1
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Ala Ser Asp Phe Leu Lys His Cys Gln Ala Asp His Leu Leu Asp
1               5                   10                  15

Glu Lys Gly Arg Ala Gln Cys Leu Leu Gln Arg Glu Met Val Gln Ser
            20                  25                  30

Leu Glu Gln Gln Leu Val Leu Glu Lys Glu Lys Leu Ser Ala Met Gln
        35                  40                  45

Ala His Leu Ala Gly Lys Met Ala Leu Thr Lys Ala Ser Ser Val Ala
    50                  55                  60

Ser Ser Asp Lys
65

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Phe Pro Ala Pro Leu Ala Pro Gly Gly Leu Tyr Leu Gly Gly
1               5                   10

<210> SEQ ID NO 3
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 4
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Leu Glu Thr Ala Lys Glu Pro Cys Met Ala Lys Phe Gly Pro Leu
1               5                   10                  15

```
Pro Ser Lys Trp Gln Met Ala Ser Ser Glu Pro Pro Cys Val Asn Lys
            20                  25                  30

Val Ser Asp Trp Lys Leu Glu Ile Leu Gln Asn Gly Leu Tyr Leu Ile
        35                  40                  45

Tyr Gly Gln Val Ala Pro Asn Ala Asn Tyr Asn Asp Val Ala Pro Phe
    50                  55                  60

Glu Val Arg Leu Tyr Lys Asn Lys Asp Met Ile Gln Thr Leu Thr Asn
65                  70                  75                  80

Lys Ser Lys Ile Gln Asn Val Gly Gly Thr Tyr Glu Leu His Val Gly
                85                  90                  95

Asp Thr Ile Asp Leu Ile Phe Asn Ser Glu His Gln Val Leu Lys Asn
            100                 105                 110

Asn Thr Tyr Trp Gly Ile Ile Leu Leu Ala Asn Pro Gln Phe Ile Ser
        115                 120                 125

<210> SEQ ID NO 5
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Ala Phe Cys Asp Gly Phe Tyr Ala Cys Tyr Met Asp Val Gly Gly
1               5                   10                  15

Gly Gly Gly Ser Met Ala Ser Asp Phe Leu Lys His Cys Gln Ala Asp
            20                  25                  30

His Leu Leu Asp Glu Lys Gly Arg Ala Gln Cys Leu Leu Gln Arg Glu
        35                  40                  45

Met Val Gln Ser Leu Glu Gln Gln Leu Val Leu Glu Lys Glu Lys Leu
    50                  55                  60

Ser Ala Met Gln Ala His Leu Ala Gly Lys Met Ala Leu Thr Lys Ala
65                  70                  75                  80

Ser Ser Val Ala Ser Ser Asp Lys Leu Glu His His His His His His
                85                  90                  95

<210> SEQ ID NO 6
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ala Phe Cys Asp Gly Phe Tyr Ala Cys Tyr Met Asp Val Gly Gly
1               5                   10                  15

Gly Gly Gly Ser Phe Pro Ala Pro Leu Ala Pro Gly Gly Leu Tyr Leu
            20                  25                  30

Gly Gly Glu Asn Leu Tyr Phe Gln Gly Met Ser Asp Lys Ile Ile His
        35                  40                  45

Leu Thr Asp Asp Ser Phe Asp Thr Asp Val Leu Lys Ala Asp Gly Ala
    50                  55                  60

Ile Leu Val Asp Phe Trp Ala Glu Trp Cys Gly Pro Cys Lys Met Ile
65                  70                  75                  80

Ala Pro Ile Leu Asp Glu Ile Ala Asp Glu Tyr Gln Gly Lys Leu Thr
                85                  90                  95
```

```
Val Ala Lys Leu Asn Ile Asp Gln Asn Pro Gly Thr Ala Pro Lys Tyr
            100                 105                 110

Gly Ile Arg Gly Ile Pro Thr Leu Leu Leu Phe Lys Asn Gly Glu Val
            115                 120                 125

Ala Ala Thr Lys Val Gly Ala Leu Ser Lys Gly Gln Leu Lys Glu Phe
            130                 135                 140

Leu Asp Ala Asn Leu Ala Leu Glu His His His His His His
145                 150                 155

<210> SEQ ID NO 7
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Ala Phe Cys Asp Gly Phe Tyr Ala Cys Tyr Met Asp Val Gly Gly
1               5                   10                  15

Gly Gly Gly Ser Val Asp Asn Lys Phe Asn Lys Glu Gln Gln Asn Ala
            20                  25                  30

Phe Tyr Glu Ile Leu His Leu Pro Asn Leu Asn Glu Glu Gln Arg Asn
        35                  40                  45

Ala Phe Ile Gln Ser Leu Lys Asp Asp Pro Ser Gln Ser Ala Asn Leu
    50                  55                  60

Leu Ala Glu Ala Lys Lys Leu Asn Asp Ala Gln Ala Pro Lys Leu Glu
65                  70                  75                  80

His His His His His His
            85

<210> SEQ ID NO 8
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Ala Phe Cys Asp Gly Phe Tyr Ala Cys Tyr Met Asp Val Gly Gly
1               5                   10                  15

Gly Gly Gly Ser Gln Leu Glu Thr Ala Lys Glu Pro Cys Met Ala Lys
            20                  25                  30

Phe Gly Pro Leu Pro Ser Lys Trp Gln Met Ala Ser Ser Glu Pro Pro
        35                  40                  45

Cys Val Asn Lys Val Ser Asp Trp Lys Leu Glu Ile Leu Gln Asn Gly
    50                  55                  60

Leu Tyr Leu Ile Tyr Gly Gln Val Ala Pro Asn Ala Asn Tyr Asn Asp
65                  70                  75                  80

Val Ala Pro Phe Glu Val Arg Leu Tyr Lys Asn Lys Asp Met Ile Gln
            85                  90                  95

Thr Leu Thr Asn Lys Ser Lys Ile Gln Asn Val Gly Gly Thr Tyr Glu
            100                 105                 110

Leu His Val Gly Asp Thr Ile Asp Leu Ile Phe Asn Ser Glu His Gln
        115                 120                 125

Val Leu Lys Asn Asn Thr Tyr Trp Gly Ile Ile Leu Leu Ala Asn Pro
    130                 135                 140
```

```
Gln Phe Ile Ser Leu Glu His His His His His
145                 150                 155
```

<210> SEQ ID NO 9
<211> LENGTH: 161
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Met Ala Phe Cys Asp Gly Phe Tyr Ala Cys Tyr Met Asp Val Gly Gly
1               5                   10                  15

Gly Gly Gly Ser Met Ala Ser Asp Phe Leu Lys His Cys Gln Ala Asp
            20                  25                  30

His Leu Leu Asp Glu Lys Gly Arg Ala Gln Cys Leu Leu Gln Arg Glu
        35                  40                  45

Met Val Gln Ser Leu Glu Gln Gln Leu Val Leu Glu Lys Glu Lys Leu
    50                  55                  60

Ser Ala Met Gln Ala His Leu Ala Gly Lys Met Ala Leu Thr Lys Ala
65                  70                  75                  80

Ser Ser Val Ala Ser Ser Asp Lys Gly Gly Gly Ser Glu Leu Val
                85                  90                  95

Asp Asn Lys Phe Asn Lys Glu Gln Gln Asn Ala Phe Tyr Glu Ile Leu
            100                 105                 110

His Leu Pro Asn Leu Asn Glu Glu Gln Arg Asn Ala Phe Ile Gln Ser
        115                 120                 125

Leu Lys Asp Asp Pro Ser Gln Ser Ala Asn Leu Leu Ala Glu Ala Lys
    130                 135                 140

Lys Leu Asn Asp Ala Gln Ala Pro Lys Leu Glu His His His His His
145                 150                 155                 160

His
```

<210> SEQ ID NO 10
<211> LENGTH: 322
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Asn
            20                  25                  30

Thr Ala Val Ala Trp Tyr Gln Gln Lys Pro Gly Lys Ala Pro Lys Leu
        35                  40                  45

Leu Ile Tyr Ser Ala Ser Phe Leu Tyr Ser Gly Val Pro Ser Arg Phe
    50                  55                  60

Ser Gly Ser Arg Ser Gly Thr Asp Phe Thr Leu Thr Ile Ser Ser Leu
65                  70                  75                  80

Gln Pro Glu Asp Phe Ala Thr Tyr Tyr Cys Gln Gln His Tyr Thr Thr
                85                  90                  95

Pro Pro Thr Phe Gly Gln Gly Thr Lys Val Glu Leu Lys Arg Ala Thr
            100                 105                 110

Pro Ser His Asn Ser His Gln Val Pro Ser Ala Gly Gly Pro Thr Ala
```

-continued

```
                115                 120                 125
Asn Ser Gly Glu Val Lys Leu Val Glu Ser Gly Gly Leu Val Gln
130                 135                 140

Pro Gly Gly Ser Leu Arg Leu Ser Cys Ala Thr Ser Gly Phe Asn Ile
145                 150                 155                 160

Lys Asp Thr Tyr Ile His Trp Val Arg Gln Ala Pro Gly Lys Gly Leu
                165                 170                 175

Glu Trp Val Ala Arg Ile Tyr Pro Thr Asn Gly Tyr Thr Arg Tyr Ala
                180                 185                 190

Asp Ser Val Lys Gly Arg Phe Thr Ile Ser Ala Asp Thr Ser Lys Asn
                195                 200                 205

Thr Ala Tyr Leu Gln Met Asn Ser Leu Arg Ala Glu Asp Thr Ala Val
210                 215                 220

Tyr Tyr Cys Ser Arg Trp Gly Gly Asp Gly Phe Tyr Ala Met Asp Tyr
225                 230                 235                 240

Trp Gly Gln Gly Thr Thr Val Thr Val Ser Ser Gly Gly Gly Gly Ser
                245                 250                 255

Val Asp Asn Lys Phe Asn Lys Glu Gln Gln Asn Ala Phe Tyr Glu Ile
                260                 265                 270

Leu His Leu Pro Asn Leu Asn Glu Glu Gln Arg Asn Ala Phe Ile Gln
                275                 280                 285

Ser Leu Lys Asp Asp Pro Ser Gln Ser Ala Asn Leu Leu Ala Glu Ala
290                 295                 300

Lys Lys Leu Asn Asp Ala Gln Ala Pro Lys Leu Glu His His His His
305                 310                 315                 320

His His
```

```
<210> SEQ ID NO 11
<211> LENGTH: 392
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Asn
                20                  25                  30

Thr Ala Val Ala Trp Tyr Gln Gln Lys Pro Gly Lys Ala Pro Lys Leu
            35                  40                  45

Leu Ile Tyr Ser Ala Ser Phe Leu Tyr Ser Gly Val Pro Ser Arg Phe
        50                  55                  60

Ser Gly Ser Arg Ser Gly Thr Asp Phe Thr Leu Thr Ile Ser Ser Leu
65                  70                  75                  80

Gln Pro Glu Asp Phe Ala Thr Tyr Tyr Cys Gln Gln His Tyr Thr Thr
                85                  90                  95

Pro Pro Thr Phe Gly Gln Gly Thr Lys Val Glu Leu Lys Arg Ala Thr
            100                 105                 110

Pro Ser His Asn Ser His Gln Val Pro Ser Ala Gly Gly Pro Thr Ala
        115                 120                 125

Asn Ser Gly Glu Val Lys Leu Val Glu Ser Gly Gly Gly Leu Val Gln
130                 135                 140

Pro Gly Gly Ser Leu Arg Leu Ser Cys Ala Thr Ser Gly Phe Asn Ile
```

```
                145                 150                 155                 160
        Lys Asp Thr Tyr Ile His Trp Val Arg Gln Ala Pro Gly Lys Gly Leu
                        165                 170                 175

Glu Trp Val Ala Arg Ile Tyr Pro Thr Asn Gly Tyr Thr Arg Tyr Ala
                        180                 185                 190

Asp Ser Val Lys Gly Arg Phe Thr Ile Ser Ala Asp Thr Ser Lys Asn
                        195                 200                 205

Thr Ala Tyr Leu Gln Met Asn Ser Leu Arg Ala Glu Asp Thr Ala Val
                        210                 215                 220

Tyr Tyr Cys Ser Arg Trp Gly Gly Asp Gly Phe Tyr Ala Met Asp Tyr
        225                 230                 235                 240

Trp Gly Gln Gly Thr Thr Val Thr Val Ser Ser Gly Gly Gly Gly Ser
                        245                 250                 255

Gln Leu Glu Thr Ala Lys Glu Pro Cys Met Ala Lys Phe Gly Pro Leu
                        260                 265                 270

Pro Ser Lys Trp Gln Met Ala Ser Ser Glu Pro Pro Cys Val Asn Lys
                        275                 280                 285

Val Ser Asp Trp Lys Leu Glu Ile Leu Gln Asn Gly Leu Tyr Leu Ile
                        290                 295                 300

Tyr Gly Gln Val Ala Pro Asn Ala Asn Tyr Asn Asp Val Ala Pro Phe
        305                 310                 315                 320

Glu Val Arg Leu Tyr Lys Asn Lys Asp Met Ile Gln Thr Leu Thr Asn
                        325                 330                 335

Lys Ser Lys Ile Gln Asn Val Gly Gly Thr Tyr Glu Leu His Val Gly
                        340                 345                 350

Asp Thr Ile Asp Leu Ile Phe Asn Ser Glu His Gln Val Leu Lys Asn
                        355                 360                 365

Asn Thr Tyr Trp Gly Ile Ile Leu Leu Ala Asn Pro Gln Phe Ile Ser
                        370                 375                 380

Leu Glu His His His His His His
        385                 390

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Phe Cys Asp Gly Phe Tyr Ala Cys Tyr Met Asp Val
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Tyr Cys Asp Gly Phe Tyr Ala Cys Tyr Met Asp Val
1               5                   10

<210> SEQ ID NO 14
<211> LENGTH: 11
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 14

Tyr Cys Phe Pro Asp Glu Glu Gly Ala Cys Tyr
1               5                   10

<210> SEQ ID NO 15
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Pro Cys Pro Ile Asn Cys Thr His Ser Cys Val Asp Leu Asp Asp Lys
1               5                   10                  15

Gly Cys Pro Ala Glu Gln Arg Ala Ser Pro Leu Thr Ser Ile
            20                  25                  30

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Tyr Cys Pro Ile Trp Lys Phe Pro Asp Glu Glu Cys Tyr
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Tyr Cys Phe Pro Asp Glu Glu Gly Ala Cys Tyr
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Tyr Cys Gly Tyr Ser Ser Thr Ser Tyr Cys Phe Val Met Asp
1               5                   10

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Tyr Cys Ala Ser Arg Asp Tyr Asp Tyr Asp Gly Arg Cys Tyr Phe Asp
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Tyr Cys Thr Arg Gly Tyr Ser Ser Thr Ser Tyr Cys Tyr Ala Met Asp
1               5                   10                  15

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Phe Cys Met Glu Glu Ser Gly Gly Asn Tyr Cys Tyr
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Tyr Cys Ala Leu Arg Gly Gly Val Tyr Trp Pro Cys Tyr
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Tyr Cys Ala Leu Thr Tyr Tyr Asp Tyr Glu Cys Phe Ala Tyr
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Tyr Cys Leu Val Trp Lys Tyr Ala Asp Ala Gly Cys Tyr
1               5                   10

<210> SEQ ID NO 25
<211> LENGTH: 5
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 25

Gly Gly Gly Gly Ser
1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Gly Gly Gly Gly Ser
1               5

<210> SEQ ID NO 27
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Glu Pro Arg Val Ile Asp Leu Trp Asp Leu Ala Gln Ser Ala Asn
1               5                   10                  15

Leu Thr Asp Lys Glu Leu Glu Ala Phe Arg Glu Glu Leu Lys His Phe
            20                  25                  30

Glu Ala Lys Ile Gln Gly Asp Gly Tyr Thr Val Lys Lys His Leu Gln
        35                  40                  45

Asp Leu Ser Gly Arg Ile Ser Arg Ala Arg His
    50                  55

<210> SEQ ID NO 28
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: F, L, I, V or Y
<220> FEATURE:
<221> NAME/KEY: MOD_RES
<222> LOCATION: (7)..(7)
<223> OTHER INFORMATION: N, Q, K or R
<220> FEATURE:
<221> NAME/KEY: MOD_RES
<222> LOCATION: (9)..(9)
<223> OTHER INFORMATION: F or Y
<220> FEATURE:
<221> NAME/KEY: MOD_RES
<222> LOCATION: (10)..(10)
<223> OTHER INFORMATION: Y, W, S or V
<220> FEATURE:
<221> NAME/KEY: MOD_RES
<222> LOCATION: (13)..(13)
<223> OTHER INFORMATION: L, F, V, Y or H
<220> FEATURE:
<221> NAME/KEY: MOD_RES
<222> LOCATION: (14)..(14)
<223> OTHER INFORMATION: H, R, D, N or K
<220> FEATURE:
```

```
<221> NAME/KEY: MOD_RES
<222> LOCATION: (22)..(22)
<223> OTHER INFORMATION: R, H, Q or K
<220> FEATURE:
<221> NAME/KEY: MOD_RES
<222> LOCATION: (23)..(23)
<223> OTHER INFORMATION: N, Q, S, E or D,
<220> FEATURE:
<221> NAME/KEY: MOD_RES
<222> LOCATION: (26)..(26)
<223> OTHER INFORMATION: I or L
<220> FEATURE:
<221> NAME/KEY: MOD_RES
<222> LOCATION: (27)..(27)
<223> OTHER INFORMATION: Q, S, E, A or K
<220> FEATURE:
<221> NAME/KEY: MOD_RES
<222> LOCATION: (33)..(33)
<223> OTHER INFORMATION: S, V, L, G or D
<220> FEATURE:
<221> NAME/KEY: MISC_FEATURE
<222> LOCATION: (38)..(38)
<223> OTHER INFORMATION: May or may not be present

<400> SEQUENCE: 28

Xaa Glu Pro Arg Val Gln Xaa Leu Xaa Xaa Leu Ala Xaa Xaa Ala Asn
1               5                   10                  15

Leu Thr Asp Lys Glu Xaa Xaa Ala Phe Xaa Xaa Glu Leu Lys His Phe
            20                  25                  30

Xaa Ala Lys Ile Gln Lys Gly Asp Gly Tyr Thr Val Lys Lys His Leu
        35                  40                  45

Gln Asp Leu Ser Gly Arg Ile Ser Arg Ala Arg His
    50                  55                  60

<210> SEQ ID NO 29
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Phe Glu Pro Arg Val Gln Asn Leu Phe Tyr Leu Ala Leu His Ala Asn
1               5                   10                  15

Leu Thr Asp Lys Glu Arg Asn Ala Phe Ile Gln Glu Leu Lys His Phe
            20                  25                  30

Ser Ala Lys Ile Gln Gly Asp Gly Tyr Thr Val Lys Lys His Leu Gln
        35                  40                  45

Asp Leu Ser Gly Arg Ile Ser Arg Ala Arg His
    50                  55

<210> SEQ ID NO 30
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Asn
            20                  25                  30

Thr Ala Val Ala Trp Tyr Gln Gln Lys Pro Gly Lys Ala Pro Lys Leu
```

35                  40                  45
Leu Ile Tyr Ser Ala Ser Phe Leu Tyr Ser Gly Val Pro Ser Arg Phe
 50                  55                  60

Ser Gly Ser Arg Ser Gly Thr Asp Phe Thr Leu Thr Ile Ser Ser Leu
 65                  70                  75                  80

Gln Pro Glu Asp Phe Ala Thr Tyr Tyr Cys Gln His Tyr Thr Thr
                 85                  90                  95

Pro Pro Thr Phe Gly Gln Gly Thr Lys Val Glu Leu Lys Arg Ala Thr
                100                 105                 110

Pro Ser His Asn Ser His Gln Val Pro Ser Ala Gly Gly Pro Thr Ala
                115                 120                 125

Asn Ser Gly Glu Val Lys Leu Val Glu Ser Gly Gly Gly Leu Val Gln
130                 135                 140

Pro Gly Gly Ser Leu Arg Leu Ser Cys Ala Thr Ser Gly Phe Asn Ile
145                 150                 155                 160

Lys Asp Thr Tyr Ile His Trp Val Arg Gln Ala Pro Gly Lys Gly Leu
                165                 170                 175

Glu Trp Val Ala Arg Ile Tyr Pro Thr Asn Gly Tyr Thr Arg Tyr Ala
                180                 185                 190

Asp Ser Val Lys Gly Arg Phe Thr Ile Ser Ala Asp Thr Ser Lys Asn
                195                 200                 205

Thr Ala Tyr Leu Gln Met Asn Ser Leu Arg Ala Glu Asp Thr Ala Val
210                 215                 220

Tyr Tyr Cys Ser Arg Trp Gly Gly Asp Gly Phe Tyr Ala Met Asp Tyr
225                 230                 235                 240

Trp Gly Gln Gly Thr Thr Val Thr Val Ser Ser
                245                 250

<210> SEQ ID NO 31
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (259)..(259)
<223> OTHER INFORMATION: F, L, I, V or Y
<220> FEATURE:
<221> NAME/KEY: MOD_RES
<222> LOCATION: (265)..(265)
<223> OTHER INFORMATION: N, Q, K or R
<220> FEATURE:
<221> NAME/KEY: MOD_RES
<222> LOCATION: (267)..(267)
<223> OTHER INFORMATION: F or Y
<220> FEATURE:
<221> NAME/KEY: MOD_RES
<222> LOCATION: (268)..(268)
<223> OTHER INFORMATION: Y, W, S or V
<220> FEATURE:
<221> NAME/KEY: MOD_RES
<222> LOCATION: (271)..(271)
<223> OTHER INFORMATION: L, F, V, Y or H
<220> FEATURE:
<221> NAME/KEY: MOD_RES
<222> LOCATION: (272)..(272)
<223> OTHER INFORMATION: H, R, D, N or K
<220> FEATURE:
<221> NAME/KEY: MOD_RES
<222> LOCATION: (280)..(280)
<223> OTHER INFORMATION: R, H, Q or K
<220> FEATURE:
<221> NAME/KEY: MOD_RES -continued

```
<222> LOCATION: (281)..(281)
<223> OTHER INFORMATION: N, Q, S, E or D,
<220> FEATURE:
<221> NAME/KEY: MOD_RES
<222> LOCATION: (284)..(284)
<223> OTHER INFORMATION: I or L
<220> FEATURE:
<221> NAME/KEY: MOD_RES
<222> LOCATION: (285)..(285)
<223> OTHER INFORMATION: Q, S, E, A or K
<220> FEATURE:
<221> NAME/KEY: MOD_RES
<222> LOCATION: (291)..(291)
<223> OTHER INFORMATION: S, V, L, G or D
<220> FEATURE:
<221> NAME/KEY: MISC_FEATURE
<222> LOCATION: (296)..(296)
<223> OTHER INFORMATION: May or may not be present

<400> SEQUENCE: 31

Met Ala Asp Ile Gln Met Thr Gln Ser Pro Ser Ser Leu Ser Ala Ser
 1               5                  10                  15

Val Gly Asp Arg Val Thr Ile Thr Cys Arg Ala Ser Gln Asp Val Asn
            20                  25                  30

Thr Ala Val Ala Trp Tyr Gln Gln Lys Pro Gly Lys Ala Pro Lys Leu
        35                  40                  45

Leu Ile Tyr Ser Ala Ser Phe Leu Tyr Ser Gly Val Pro Ser Arg Phe
    50                  55                  60

Ser Gly Ser Arg Ser Gly Thr Asp Phe Thr Leu Thr Ile Ser Ser Leu
65                  70                  75                  80

Gln Pro Glu Asp Phe Ala Thr Tyr Tyr Cys Gln Gln His Tyr Thr Thr
                85                  90                  95

Pro Pro Thr Phe Gly Gln Gly Thr Lys Val Glu Leu Lys Arg Ala Thr
            100                 105                 110

Pro Ser His Asn Ser His Gln Val Pro Ser Ala Gly Gly Pro Thr Ala
        115                 120                 125

Asn Ser Gly Glu Val Lys Leu Val Glu Ser Gly Gly Gly Leu Val Gln
    130                 135                 140

Pro Gly Gly Ser Leu Arg Leu Ser Cys Ala Thr Ser Gly Phe Asn Ile
145                 150                 155                 160

Lys Asp Thr Tyr Ile His Trp Val Arg Gln Ala Pro Gly Lys Gly Leu
                165                 170                 175

Glu Trp Val Ala Arg Ile Tyr Pro Thr Asn Gly Tyr Thr Arg Tyr Ala
            180                 185                 190

Asp Ser Val Lys Gly Arg Phe Thr Ile Ser Ala Asp Thr Ser Lys Asn
        195                 200                 205

Thr Ala Tyr Leu Gln Met Asn Ser Leu Arg Ala Glu Asp Thr Ala Val
    210                 215                 220

Tyr Tyr Cys Ser Arg Trp Gly Gly Asp Gly Phe Tyr Ala Met Asp Tyr
225                 230                 235                 240

Trp Gly Gln Gly Thr Thr Val Thr Val Ser Ser Gly Gly Gly Gly Ser
                245                 250                 255

Val Asp Xaa Glu Pro Arg Val Gln Xaa Leu Xaa Xaa Leu Ala Xaa Xaa
            260                 265                 270

Ala Asn Leu Thr Asp Lys Glu Xaa Xaa Ala Phe Xaa Xaa Glu Leu Lys
        275                 280                 285

His Phe Xaa Ala Lys Ile Gln Lys Gly Asp Gly Tyr Thr Val Lys Lys
    290                 295                 300

His Leu Gln Asp Leu Ser Gly Arg Ile Ser Arg Ala Arg His Leu Glu
```

His His His His His His
            325

<210> SEQ ID NO 32
<211> LENGTH: 325
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Asn
            20                  25                  30

Thr Ala Val Ala Trp Tyr Gln Gln Lys Pro Gly Lys Ala Pro Lys Leu
        35                  40                  45

Leu Ile Tyr Ser Ala Ser Phe Leu Tyr Ser Gly Val Pro Ser Arg Phe
    50                  55                  60

Ser Gly Ser Arg Ser Gly Thr Asp Phe Thr Leu Thr Ile Ser Ser Leu
65                  70                  75                  80

Gln Pro Glu Asp Phe Ala Thr Tyr Tyr Cys Gln Gln His Tyr Thr Thr
                85                  90                  95

Pro Pro Thr Phe Gly Gln Gly Thr Lys Val Glu Leu Lys Arg Ala Thr
            100                 105                 110

Pro Ser His Asn Ser His Gln Val Pro Ser Ala Gly Gly Pro Thr Ala
        115                 120                 125

Asn Ser Gly Glu Val Lys Leu Val Glu Ser Gly Gly Gly Leu Val Gln
    130                 135                 140

Pro Gly Gly Ser Leu Arg Leu Ser Cys Ala Thr Ser Gly Phe Asn Ile
145                 150                 155                 160

Lys Asp Thr Tyr Ile His Trp Val Arg Gln Ala Pro Gly Lys Gly Leu
                165                 170                 175

Glu Trp Val Ala Arg Ile Tyr Pro Thr Asn Gly Tyr Thr Arg Tyr Ala
            180                 185                 190

Asp Ser Val Lys Gly Arg Phe Thr Ile Ser Ala Asp Thr Ser Lys Asn
        195                 200                 205

Thr Ala Tyr Leu Gln Met Asn Ser Leu Arg Ala Glu Asp Thr Ala Val
    210                 215                 220

Tyr Tyr Cys Ser Arg Trp Gly Gly Asp Gly Phe Tyr Ala Met Asp Tyr
225                 230                 235                 240

Trp Gly Gln Gly Thr Thr Val Thr Val Ser Ser Gly Gly Gly Gly Ser
                245                 250                 255

Val Asp Phe Glu Pro Arg Val Gln Asn Leu Phe Tyr Leu Ala Leu His
            260                 265                 270

Ala Asn Leu Thr Asp Lys Glu Arg Asn Ala Phe Ile Gln Glu Leu Lys
        275                 280                 285

His Phe Ser Ala Lys Ile Gln Gly Asp Gly Tyr Thr Val Lys Lys His
    290                 295                 300

Leu Gln Asp Leu Ser Gly Arg Ile Ser Arg Ala Arg His Leu Glu His
305                 310                 315                 320

His His His His
            325

-continued

```
<210> SEQ ID NO 33
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (259)..(259)
<223> OTHER INFORMATION: F, L, I, V or Y
<220> FEATURE:
<221> NAME/KEY: MOD_RES
<222> LOCATION: (265)..(265)
<223> OTHER INFORMATION: N, Q, K or R
<220> FEATURE:
<221> NAME/KEY: MOD_RES
<222> LOCATION: (267)..(267)
<223> OTHER INFORMATION: F or Y
<220> FEATURE:
<221> NAME/KEY: MOD_RES
<222> LOCATION: (268)..(268)
<223> OTHER INFORMATION: Y, W, S or V
<220> FEATURE:
<221> NAME/KEY: MOD_RES
<222> LOCATION: (271)..(271)
<223> OTHER INFORMATION: L, F, V, Y or H
<220> FEATURE:
<221> NAME/KEY: MOD_RES
<222> LOCATION: (272)..(272)
<223> OTHER INFORMATION: H, R, D, N or K
<220> FEATURE:
<221> NAME/KEY: MOD_RES
<222> LOCATION: (280)..(280)
<223> OTHER INFORMATION: R, H, Q or K
<220> FEATURE:
<221> NAME/KEY: MOD_RES
<222> LOCATION: (281)..(281)
<223> OTHER INFORMATION: N, Q, S, E or D,
<220> FEATURE:
<221> NAME/KEY: MOD_RES
<222> LOCATION: (284)..(284)
<223> OTHER INFORMATION: I or L
<220> FEATURE:
<221> NAME/KEY: MOD_RES
<222> LOCATION: (285)..(285)
<223> OTHER INFORMATION: Q, S, E, A or K
<220> FEATURE:
<221> NAME/KEY: MOD_RES
<222> LOCATION: (291)..(291)
<223> OTHER INFORMATION: S, V, L, G or D
<220> FEATURE:
<221> NAME/KEY: MISC_FEATURE
<222> LOCATION: (296)..(296)
<223> OTHER INFORMATION: May or may not be present

<400> SEQUENCE: 33

Met Ala Asp Ile Gln Met Thr Gln Ser Pro Ser Ser Leu Ser Ala Ser
1               5                  10                  15

Val Gly Asp Arg Val Thr Ile Thr Cys Arg Ala Ser Gln Asp Val Asn
            20                  25                  30

Thr Ala Val Ala Trp Tyr Gln Gln Lys Pro Gly Lys Ala Pro Lys Leu
        35                  40                  45

Leu Ile Tyr Ser Ala Ser Phe Leu Tyr Ser Gly Val Pro Ser Arg Phe
    50                  55                  60

Ser Gly Ser Arg Ser Gly Thr Asp Phe Thr Leu Thr Ile Ser Ser Leu
65                  70                  75                  80

Gln Pro Glu Asp Phe Ala Thr Tyr Tyr Cys Gln Gln His Tyr Thr Thr
                85                  90                  95

Pro Pro Thr Phe Gly Gln Gly Thr Lys Val Glu Leu Lys Arg Ala Thr
            100                 105                 110
```

Pro Ser His Asn Ser His Gln Val Pro Ser Ala Gly Gly Pro Thr Ala
            115                 120                 125

Asn Ser Gly Glu Val Lys Leu Val Glu Ser Gly Gly Gly Leu Val Gln
    130                 135                 140

Pro Gly Gly Ser Leu Arg Leu Ser Cys Ala Thr Ser Gly Phe Asn Ile
145                 150                 155                 160

Lys Asp Thr Tyr Ile His Trp Val Arg Gln Ala Pro Gly Lys Gly Leu
                165                 170                 175

Glu Trp Val Ala Arg Ile Tyr Pro Thr Asn Gly Tyr Thr Arg Tyr Ala
            180                 185                 190

Asp Ser Val Lys Gly Arg Phe Thr Ile Ser Ala Asp Thr Ser Lys Asn
            195                 200                 205

Thr Ala Tyr Leu Gln Met Asn Ser Leu Arg Ala Glu Asp Thr Ala Val
    210                 215                 220

Tyr Tyr Cys Ser Arg Trp Gly Asp Gly Phe Tyr Ala Met Asp Tyr
225                 230                 235                 240

Trp Gly Gln Gly Thr Thr Val Thr Val Ser Ser Gly Gly Gly Gly Ser
                245                 250                 255

Val Asp Xaa Glu Pro Arg Val Gln Xaa Leu Xaa Xaa Leu Ala Xaa Xaa
            260                 265                 270

Ala Asn Leu Thr Asp Lys Glu Xaa Xaa Ala Phe Xaa Xaa Glu Leu Lys
    275                 280                 285

His Phe Xaa Ala Lys Ile Gln Lys Gly Asp Gly Tyr Thr Val Lys Lys
    290                 295                 300

His Leu Gln Asp Leu Ser Gly Arg Ile Ser Arg Ala Arg His Leu Glu
305                 310                 315                 320

Gly Gly Gly Gly Ser Gln Asp Pro Tyr Val Lys Glu Ala Glu Asn Leu
                325                 330                 335

Lys Lys Tyr Phe Asn Ala Gly His Ser Asp Val Ala Asp Asn Gly Thr
                340                 345                 350

Leu Phe Leu Gly Ile Leu Lys Asn Trp Lys Glu Ser Asp Arg Lys
            355                 360                 365

Ile Met Gln Ser Gln Ile Val Ser Phe Tyr Phe Lys Leu Phe Lys Asn
    370                 375                 380

Phe Lys Asp Asp Gln Ser Ile Gln Lys Ser Val Glu Thr Ile Lys Glu
385                 390                 395                 400

Asp Met Asn Val Lys Phe Phe Asn Ser Asn Lys Lys Arg Asp Asp
                405                 410                 415

Phe Glu Lys Leu Thr Asn Tyr Ser Val Thr Asp Leu Asn Val Gln Arg
            420                 425                 430

Lys Ala Ile His Glu Leu Ile Gln Val Met Ala Glu Leu Ser Pro Ala
            435                 440                 445

Ala Lys Thr Gly Lys Arg Lys Arg Ser Gln Leu Glu His His His His
    450                 455                 460

His His
465

<210> SEQ ID NO 34
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

```
<221> NAME/KEY: MOD_RES
<222> LOCATION: (259)..(259)
<223> OTHER INFORMATION: F, L, I, V or Y
<220> FEATURE:
<221> NAME/KEY: MOD_RES
<222> LOCATION: (265)..(265)
<223> OTHER INFORMATION: N, Q, K or R
<220> FEATURE:
<221> NAME/KEY: MOD_RES
<222> LOCATION: (267)..(267)
<223> OTHER INFORMATION: F or Y
<220> FEATURE:
<221> NAME/KEY: MOD_RES
<222> LOCATION: (268)..(268)
<223> OTHER INFORMATION: Y, W, S or V
<220> FEATURE:
<221> NAME/KEY: MOD_RES
<222> LOCATION: (271)..(271)
<223> OTHER INFORMATION: L, F, V, Y or H
<220> FEATURE:
<221> NAME/KEY: MOD_RES
<222> LOCATION: (272)..(272)
<223> OTHER INFORMATION: H, R, D, N or K
<220> FEATURE:
<221> NAME/KEY: MOD_RES
<222> LOCATION: (280)..(280)
<223> OTHER INFORMATION: R, H, Q or K
<220> FEATURE:
<221> NAME/KEY: MOD_RES
<222> LOCATION: (281)..(281)
<223> OTHER INFORMATION: N, Q, S, E or D,
<220> FEATURE:
<221> NAME/KEY: MOD_RES
<222> LOCATION: (284)..(284)
<223> OTHER INFORMATION: I or L
<220> FEATURE:
<221> NAME/KEY: MOD_RES
<222> LOCATION: (285)..(285)
<223> OTHER INFORMATION: Q, S, E, A or K
<220> FEATURE:
<221> NAME/KEY: MOD_RES
<222> LOCATION: (291)..(291)
<223> OTHER INFORMATION: S, V, L, G or D
<220> FEATURE:
<221> NAME/KEY: MISC_FEATURE
<222> LOCATION: (296)..(296)
<223> OTHER INFORMATION: May or may not be present

<400> SEQUENCE: 34

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Asn
            20                  25                  30

Thr Ala Val Ala Trp Tyr Gln Gln Lys Pro Gly Lys Ala Pro Lys Leu
        35                  40                  45

Leu Ile Tyr Ser Ala Ser Phe Leu Tyr Ser Gly Val Pro Ser Arg Phe
    50                  55                  60

Ser Gly Ser Arg Ser Gly Thr Asp Phe Thr Leu Thr Ile Ser Ser Leu
65                  70                  75                  80

Gln Pro Glu Asp Phe Ala Thr Tyr Tyr Cys Gln Gln His Tyr Thr Thr
                85                  90                  95

Pro Pro Thr Phe Gly Gln Gly Thr Lys Val Glu Leu Lys Arg Ala Thr
            100                 105                 110

Pro Ser His Asn Ser His Gln Val Pro Ser Ala Gly Gly Pro Thr Ala
        115                 120                 125

Asn Ser Gly Glu Val Lys Leu Val Glu Ser Gly Gly Gly Leu Val Gln
    130                 135                 140

Pro Gly Gly Ser Leu Arg Leu Ser Cys Ala Thr Ser Gly Phe Asn Ile
145                 150                 155                 160
```

```
Lys Asp Thr Tyr Ile His Trp Val Arg Gln Ala Pro Gly Lys Gly Leu
            165                 170                 175

Glu Trp Val Ala Arg Ile Tyr Pro Thr Asn Gly Tyr Thr Arg Tyr Ala
        180                 185                 190

Asp Ser Val Lys Gly Arg Phe Thr Ile Ser Ala Asp Thr Ser Lys Asn
    195                 200                 205

Thr Ala Tyr Leu Gln Met Asn Ser Leu Arg Ala Glu Asp Thr Ala Val
210                 215                 220

Tyr Tyr Cys Ser Arg Trp Gly Asp Gly Phe Tyr Ala Met Asp Tyr
225                 230                 235                 240

Trp Gly Gln Gly Thr Thr Val Thr Val Ser Ser Gly Gly Gly Gly Ser
            245                 250                 255

Val Asp Xaa Glu Pro Arg Val Gln Xaa Leu Xaa Xaa Leu Ala Xaa Xaa
        260                 265                 270

Ala Asn Leu Thr Asp Lys Glu Xaa Xaa Ala Phe Xaa Xaa Glu Leu Lys
    275                 280                 285

His Phe Xaa Ala Lys Ile Gln Lys Gly Asp Gly Tyr Thr Val Lys Lys
        290                 295                 300

His Leu Gln Asp Leu Ser Gly Arg Ile Ser Arg Ala Arg His Leu Glu
305                 310                 315                 320

Gly Gly Gly Gly Ser His Gly Thr Val Ile Glu Ser Leu Glu Ser Leu
            325                 330                 335

Asn Asn Tyr Phe Asn Ser Ser Gly Ile Asp Val Glu Glu Lys Ser Leu
        340                 345                 350

Phe Leu Asp Ile Trp Arg Asn Trp Gln Lys Asp Gly Asp Met Lys Ile
    355                 360                 365

Leu Gln Ser Gln Ile Ile Ser Phe Tyr Leu Arg Leu Phe Glu Val Leu
370                 375                 380

Lys Asp Asn Gln Ala Ile Ser Asn Asn Ile Ser Val Ile Glu Ser His
385                 390                 395                 400

Leu Ile Thr Thr Phe Phe Ser Asn Ser Lys Ala Lys Lys Asp Ala Phe
            405                 410                 415

Met Ser Ile Ala Lys Phe Glu Val Asn Asn Pro Gln Val Gln Arg Gln
        420                 425                 430

Ala Phe Asn Glu Leu Ile Arg Val Val His Gln Leu Leu Pro Glu Ser
    435                 440                 445

Ser Leu Arg Lys Arg Lys Arg Ser Arg Leu Glu His His His His His
450                 455                 460

His
465

<210> SEQ ID NO 35
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Asn
            20                  25                  30

Thr Ala Val Ala Trp Tyr Gln Gln Lys Pro Gly Lys Ala Pro Lys Leu
```

```
            35                  40                  45
Leu Ile Tyr Ser Ala Ser Phe Leu Tyr Ser Gly Val Pro Ser Arg Phe
 50                  55                  60

Ser Gly Ser Arg Ser Gly Thr Asp Phe Thr Leu Thr Ile Ser Ser Leu
 65                  70                  75                  80

Gln Pro Glu Asp Phe Ala Thr Tyr Tyr Cys Gln Gln His Tyr Thr Thr
                 85                  90                  95

Pro Pro Thr Phe Gly Gln Gly Thr Lys Val Glu Leu Lys Arg Ala Thr
                100                 105                 110

Pro Ser His Asn Ser His Gln Val Pro Ser Ala Gly Gly Pro Thr Ala
                115                 120                 125

Asn Ser Gly Glu Val Lys Leu Val Glu Ser Gly Gly Gly Leu Val Gln
130                 135                 140

Pro Gly Gly Ser Leu Arg Leu Ser Cys Ala Thr Ser Gly Phe Asn Ile
145                 150                 155                 160

Lys Asp Thr Tyr Ile His Trp Val Arg Gln Ala Pro Gly Lys Gly Leu
                165                 170                 175

Glu Trp Val Ala Arg Ile Tyr Pro Thr Asn Gly Tyr Thr Arg Tyr Ala
                180                 185                 190

Asp Ser Val Lys Gly Arg Phe Thr Ile Ser Ala Asp Thr Ser Lys Asn
                195                 200                 205

Thr Ala Tyr Leu Gln Met Asn Ser Leu Arg Ala Glu Asp Thr Ala Val
210                 215                 220

Tyr Tyr Cys Ser Arg Trp Gly Asp Gly Phe Tyr Ala Met Asp Tyr
225                 230                 235                 240

Trp Gly Gln Gly Thr Thr Val Thr Val Ser Ser Gly Gly Gly Gly Ser
                245                 250                 255

Val Asp Phe Glu Pro Arg Val Gln Asn Leu Phe Tyr Leu Ala Leu His
                260                 265                 270

Ala Asn Leu Thr Asp Lys Glu Arg Asn Ala Phe Ile Gln Glu Leu Lys
                275                 280                 285

His Phe Ser Ala Lys Ile Gln Gly Asp Gly Tyr Thr Val Lys Lys His
                290                 295                 300

Leu Gln Asp Leu Ser Gly Arg Ile Ser Arg Ala Arg His Leu Glu Gly
305                 310                 315                 320

Gly Gly Gly Ser Gln Asp Pro Tyr Val Lys Glu Ala Glu Asn Leu Lys
                325                 330                 335

Lys Tyr Phe Asn Ala Gly His Ser Asp Val Ala Asp Asn Gly Thr Leu
                340                 345                 350

Phe Leu Gly Ile Leu Lys Asn Trp Lys Glu Glu Ser Asp Arg Lys Ile
                355                 360                 365

Met Gln Ser Gln Ile Val Ser Phe Tyr Phe Lys Leu Phe Lys Asn Phe
                370                 375                 380

Lys Asp Asp Gln Ser Ile Gln Lys Ser Val Glu Thr Ile Lys Glu Asp
385                 390                 395                 400

Met Asn Val Lys Phe Phe Asn Ser Asn Lys Lys Lys Arg Asp Asp Phe
                405                 410                 415

Glu Lys Leu Thr Asn Tyr Ser Val Thr Asp Leu Asn Val Gln Arg Lys
                420                 425                 430

Ala Ile His Glu Leu Ile Gln Val Met Ala Glu Leu Ser Pro Ala Ala
                435                 440                 445

Lys Thr Gly Lys Arg Lys Arg Ser Gln Leu Glu His His His His
450                 455                 460
```

His
465

<210> SEQ ID NO 36
<211> LENGTH: 464
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Asn
            20                  25                  30

Thr Ala Val Ala Trp Tyr Gln Gln Lys Pro Gly Lys Ala Pro Lys Leu
        35                  40                  45

Leu Ile Tyr Ser Ala Ser Phe Leu Tyr Ser Gly Val Pro Ser Arg Phe
    50                  55                  60

Ser Gly Ser Arg Ser Gly Thr Asp Phe Thr Leu Thr Ile Ser Ser Leu
65                  70                  75                  80

Gln Pro Glu Asp Phe Ala Thr Tyr Tyr Cys Gln Gln His Tyr Thr Thr
                85                  90                  95

Pro Pro Thr Phe Gly Gln Gly Thr Lys Val Glu Leu Lys Arg Ala Thr
            100                 105                 110

Pro Ser His Asn Ser His Gln Val Pro Ser Ala Gly Gly Pro Thr Ala
        115                 120                 125

Asn Ser Gly Glu Val Lys Leu Val Glu Ser Gly Gly Gly Leu Val Gln
    130                 135                 140

Pro Gly Gly Ser Leu Arg Leu Ser Cys Ala Thr Ser Gly Phe Asn Ile
145                 150                 155                 160

Lys Asp Thr Tyr Ile His Trp Val Arg Gln Ala Pro Gly Lys Gly Leu
                165                 170                 175

Glu Trp Val Ala Arg Ile Tyr Pro Thr Asn Gly Tyr Thr Arg Tyr Ala
            180                 185                 190

Asp Ser Val Lys Gly Arg Phe Thr Ile Ser Ala Asp Thr Ser Lys Asn
        195                 200                 205

Thr Ala Tyr Leu Gln Met Asn Ser Leu Arg Ala Glu Asp Thr Ala Val
    210                 215                 220

Tyr Tyr Cys Ser Arg Trp Gly Asp Gly Phe Tyr Ala Met Asp Tyr
225                 230                 235                 240

Trp Gly Gln Gly Thr Thr Val Thr Val Ser Ser Gly Gly Gly Gly Ser
            245                 250                 255

Val Asp Phe Glu Pro Arg Val Gln Asn Leu Phe Tyr Leu Ala Leu His
        260                 265                 270

Ala Asn Leu Thr Asp Lys Glu Arg Asn Ala Phe Ile Gln Glu Leu Lys
    275                 280                 285

His Phe Ser Ala Lys Ile Gln Gly Asp Gly Tyr Thr Val Lys Lys His
290                 295                 300

Leu Gln Asp Leu Ser Gly Arg Ile Ser Arg Ala Arg His Leu Glu Gly
305                 310                 315                 320

Gly Gly Gly Ser His Gly Thr Val Ile Glu Ser Leu Glu Ser Leu Asn
                325                 330                 335

Asn Tyr Phe Asn Ser Ser Gly Ile Asp Val Glu Glu Lys Ser Leu Phe

```
                        340                 345                 350
Leu Asp Ile Trp Arg Asn Trp Gln Lys Asp Gly Asp Met Lys Ile Leu
                355                 360                 365

Gln Ser Gln Ile Ile Ser Phe Tyr Leu Arg Leu Phe Glu Val Leu Lys
        370                 375                 380

Asp Asn Gln Ala Ile Ser Asn Asn Ile Ser Val Ile Glu Ser His Leu
385                 390                 395                 400

Ile Thr Thr Phe Phe Ser Asn Ser Lys Ala Lys Lys Asp Ala Phe Met
                405                 410                 415

Ser Ile Ala Lys Phe Glu Val Asn Asn Pro Gln Val Gln Arg Gln Ala
            420                 425                 430

Phe Asn Glu Leu Ile Arg Val Val His Gln Leu Leu Pro Glu Ser Ser
        435                 440                 445

Leu Arg Lys Arg Lys Arg Ser Arg Leu Glu His His His His His His
    450                 455                 460

<210> SEQ ID NO 37
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gly Ala Gly Thr Met Val Lys Gln Ile Glu Ser Lys Thr Ala Phe Gln
1               5                   10                  15

Lys Ala Leu Lys Ala Ala Gly Asp Lys Leu Val Val Val Asp Phe Ser
            20                  25                  30

Ala Thr Trp Cys Gly Pro Cys Lys Met Ile Lys Pro Phe Phe His Ser
        35                  40                  45

Leu Ser Glu Lys Tyr Ser Asn Val Ile Phe Leu Glu Val Asp Val Asp
    50                  55                  60

Asp Cys Gln Asp Val Ala Ser Glu Cys Glu Val Lys Cys Met Pro Thr
65                  70                  75                  80

Phe Gln Phe Phe Lys Lys Gly Gln Lys Val Gly Glu Phe Ser Gly Ala
                85                  90                  95

Asn Lys Lys Lys Leu Glu Ala Thr Ile Asn Lys Leu Val
            100                 105

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 38

His His His His His His
1               5
```

IGG BINDING PEPTIDES AND MULTIFUNCTIONAL ANTIGEN-BINDING PROTEINS COMPRISING THE SAME

CROSS REFERENCE TO RELATED APPLICATIONS

This application claims priority to and the benefit of U.S. Patent Application No. 62/351,335, filed Jun. 17, 2016, and International Patent Application No. PCT/EP2017/037881, filed Jun. 16, 2017, the entireties of which are incorporated herein by reference.

GOVERNMENT RIGHTS

This invention was made with government support under grant number R01 CA149425-03 awarded by the National Institutes of Health (NIH). The government has certain rights in the invention.

TECHNICAL FIELD

Disclosed herein are novel IgG binding peptides and multifunctional antigen-binding proteins comprising the same.

BACKGROUND

Since hybridoma technology enabled long-lived hybridoma production of monoclonal antibodies in the mid-1970's, scientist and clinicians have been trying to harvest their therapeutic potential to treat diseases. Over the years, science has pushed back the frontiers of antibody technology, allowing for the development of chimeric antibodies, humanized antibodies, and immunologically functional antibody fragments, such as Fabs and diabodies. Today, there are numerous antibody therapeutics used to treat diseases such as cancer, infectious diseases, and autoimmune disorders, just to name a few. In addition to existing therapeutics, more are on the horizon and the scientific community is working feverishly to develop new and/or more effective antibody-based therapeutics.

While antibody therapeutics have proven successful in recent years, with at least 25 such therapeutics having gained FDA approval, they are not without drawbacks. Some drawbacks to antibodies include their large size (approximately 150 kD) and that they often require proper post-translational processing. The large size of antibodies can reduce their ability to target certain diseases, such as cancer or neurological disorders, which may require crossing the blood-brain barrier. The fact that many antibodies require proper post-translational processing by a eukaryotic cell often requires that antibody therapeutics be produced in, and subsequently purified from, mammalian cell culture, which can hinder total antibody production and increase production costs, relative to proteins produced in bacteria.

To overcome some of the drawbacks of antibodies, non-antibody synthetic proteins have been developed. Some examples of non-antibody synthetic proteins include antibody fragments, such as Fabs, scFvs, diabodies, Affibodies®, and Nanobodies®, to name a few. Proteins such as these, while smaller than antibodies and useful for some applications, often do not have the ability to interact with antibody receptors, such as the Fc receptor, expressed by immune effector cells, which can enhance the activity of the immune system.

SUMMARY

Disclosed herein are novel multifunctional recombinant protein scaffolds that bind to IgG. The multifunctional recombinant protein scaffolds can comprise, consist of, or consist essentially of a polypeptide that is at least: (a) 90% identical to huZZ as set forth in SEQ ID NO:28 or (b) 90% identical to huZZ1 as set forth in SEQ ID NO:29.

Also disclosed herein are multifunctional antigen-binding proteins comprising at least one multifunctional recombinant protein scaffold that binds to IgG and at least one antigen-specific binding domain, wherein the at least one multifunctional recombinant protein scaffold that binds to IgG comprises a human polypeptide that contains mutations that enable the peptide to mimic the IgG binding domain of protein A, and wherein the at least one antigen-specific binding domain comprises an antigen-specific peptide, an antigen-specific antibody or fragment thereof, or a combination thereof.

The disclosed multifunctional antigen-binding proteins are made of at least one multifunctional recombinant protein scaffold or framework segment that can be linked to at least one antigen-specific polypeptide sequence, known as an antigen-specific binding domain, to form a multifunctional antigen-binding protein. The recombinant protein scaffolds described herein can confer desirable functional characteristics such as the ability to bind to the fragment crystallizable (Fc) region of an antibody, thus enabling the multifunctional antigen-binding protein to bind a particular antigen and an Fc receptor simultaneously.

The at least one multifunctional recombinant protein scaffold that binds to IgG comprises a human polypeptide that contains mutations that enable the peptide to mimic the IgG binding domain of protein A, a *Staphylococcus aureus* cell wall component that has the ability to bind to certain antibody isotypes. In some embodiments, the at least one multifunctional recombinant protein scaffold that binds to IgG can comprise a humanized protein A IgG binding domain. In some embodiments, the at least one multifunctional recombinant protein scaffold that binds to IgG can comprise a portion of an alpha2-macroglobulin receptor-associated protein. The at least one multifunctional recombinant protein scaffold that binds to IgG can be derived from an un-mutated portion of the alpha2-macroglobulin receptor-associated protein that comprises SEQ ID NO:27. Accordingly, the multifunctional antigen-binding protein can comprise at least one multifunctional recombinant protein scaffold that binds to IgG, said at least one multifunctional recombinant protein scaffold that binds to IgG being derived from an un-mutated portion of the alpha2-macroglobulin receptor-associated protein that comprises SEQ ID NO:27, and at least one antigen-specific binding domain. Alternatively, the at least one multifunctional recombinant protein scaffold that binds to IgG can be derived from mutated portion of the alpha2-macroglobulin receptor-associated protein. For example, the at least one multifunctional recombinant protein scaffold can comprise a polypeptide that is at least 90% identical to huZZ as set forth in SEQ ID NO:28 or a polypeptide that is at least 90% identical to huZZ1 as set forth in SEQ ID NO:29.

The multifunctional antigen-binding protein can comprise at least one multifunctional recombinant protein scaffold that binds to IgG, said at least one multifunctional recombinant protein scaffold that binds to IgG comprising a polypeptide that is at least 90% identical to huZZ as set forth in SEQ ID NO:28, and at least one antigen-specific binding domain. In some aspects, the at least one multifunctional recombinant protein scaffold that binds to IgG comprising a polypeptide that is at least 90% identical to huZZ1 as set forth in SEQ ID NO:29. In some aspects, the antigen-specific binding domain can be an antigen-specific peptide, including a polypeptide that is at least 90% identical to any one of SEQ ID NOs:12-24. In other aspects, the antigen-specific binding domain can be an antigen-specific antibody, including a polypeptide that is at least 90% identical to 4D5scFv as set forth in SEQ ID NO:30.

Also provided are polynucleotides encoding the disclosed multifunctional antigen-binding proteins. In some embodiments, the polynucleotide can encode a multifunctional antigen-binding protein that comprises, consists of, or consists essentially of the amino acid sequence that is at least 90% identical to SEQ ID NOs:31-36.

Vectors encoding the polynucleotides and cells genetically engineered to express the disclosed vectors are also provided. For the sake of brevity, only a limited number of vectors having the described polynucleotide sequences are provided; however, alternative vector and polynucleotide combinations for expressing the disclosed antigen-binding proteins will be apparent to those with sufficient skill in the art to understand the degeneracy of the genetic code. Additionally, it is fully contemplated that the disclosed vectors can be used to transform prokaryotic and/or eukaryotic cells to facilitate expression of the described antigen-binding proteins. In some embodiments the described vectors are used to facilitate protein expression in bacteria, such as *E. coli*. While any *E. coli* strain can be used to express the proteins described herein, some preferred strains include: BL21 (DE3), BL21-CodonPlus® (DE3)-RP, BL21-Codon-Plus® (DE3)-RIL, BL21-(DE3)-pLysS (Stratagene). Eukaryotic cells can also be used with the described vectors to facilitate protein expression. While those of skill in the art will recognize that a wide variety of eukaryotic cells will be suitable for this purpose, some preferred embodiments include mammalian cells and insect cells. For example, in one embodiment Chinese hamster ovary (CHO) cells can be used with the described vectors to facilitate expression of the multifunctional antigen-binding proteins provided herein. In alternative embodiments, insect cells, such as Sf9 cells or S2 cells, can be used to with the described vectors to facilitate expression of the multifunctional antigen-binding proteins provided herein. Furthermore, those of skill in the art will understand that alternative vectors, not expressly disclosed herein, can be used for the same purpose of expressing, or replicating nucleic acids encoding, the described multifunctional antigen-binding proteins.

Also described herein are compositions comprising any of the disclosed multifunctional antigen-binding protein and a pharmaceutically acceptable carrier. Such compositions can be used to administer the described antigen-binding proteins to a subject or store or to maintain the described antigen-binding proteins. Any of the described antigen-binding proteins can be used to produce such compositions, which may include more than one of the disclosed antigen-binding proteins. In addition, such compositions can include other agents, such as therapeutic agents, preservatives, antimicrobial agents, and the like.

Methods of using the described multifunctional antigen-binding proteins are also provided. For example, multifunctional antigen-binding proteins may be used to treat or prevent disease in a subject. The described methods of treating or preventing disease can be used to administer compositions, having multifunctional antigen-binding proteins, to a subject in need of such treatment.

Also disclosed are methods for detecting an antigen of interest using the multifunctional antigen-binding proteins disclosed herein. Such methods are applicable to antigen detection in a subject, in a sample obtained from a subject, ex vivo or in vitro.

BRIEF DESCRIPTION OF THE DRAWINGS

The summary, as well as the following detailed description, is further understood when read in conjunction with the appended drawings. For the purpose of illustrating the disclosed compositions and methods, there are shown in the drawings exemplary embodiments of the compositions and methods; however, the compositions and methods are not limited to the specific embodiments disclosed. In the drawings:

FIG. 2, comprising In FIG. 2A, only the secondary antibody was used. The FITC labeled antibody could only be captured when 4D5scFvZZ or 4D5scFv-huZZ was presented to the cells.

FIG. 3, comprising

FIG. 4, comprising FIGS. 4A-4C, illustrates that huZZ can form a complex with Fc in solution. (FIG. 4A) Binding of 293T-expressed 4D5scFv-huZZ to h4D5 (left), m4D5 (middle), and mF77 (right). (FIG. 4B) Elution of 4D5scFv-huZZ (green line), Fc (red line) and mixture of 4D5scFv-huZZ and Fc from a size-exclusion FPLC column Superdex 200. (FIG. 4C) Fractions of 4-11 of the elution of the 4D5scFv-huZZ and Fc mixture were analyzed by SDS-PAGE. Both 4D5scFv-huZZ and Fc bands could be seen in these fractions FIG. 5, comprising FIGS. 5A-5B, illustrates that huZZ containing multifunctional antigen-binding proteins had in vitro and in vivo activity comparable to the original ZZ containing multifunctional antigen-binding proteins. (FIG. 5A) Proliferation of T6-17 cells in the presence of 4D5scFv-ZZ-mIFN or 4D5scfv-huZZ-mIFN. (FIG. 5B) In vivo activity of 4D5scFv-ZZ-mIFN and 4D5scFv-huZZ-mIFN in CT26-HER2 tumor implanted in BALB/c.

DETAILED DESCRIPTION OF ILLUSTRATIVE EMBODIMENTS

Figures 1A, 1B:
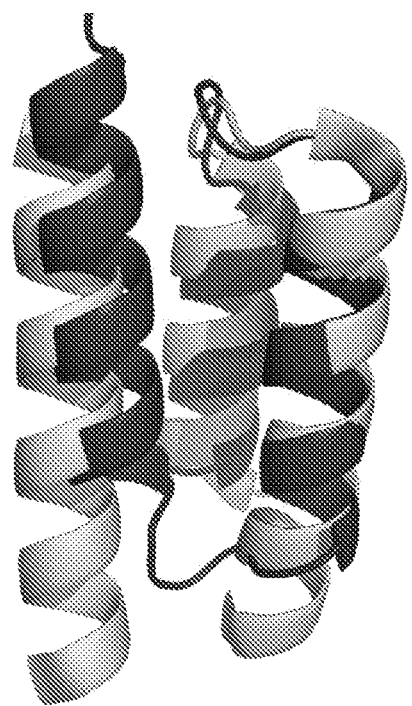
FIG. 1A illustrates a three dimension structure alignment of IgG binding domain in Protein A (Chain G of PDB: 1DEE, dark) with an α-helix region in α 2-macroglobulin receptor-associated protein (PDB: 2FCW, light)
FIG. 1B illustrates an alignment of the 2FCW template with an exemplary huZZ domain.
Figure 2A:
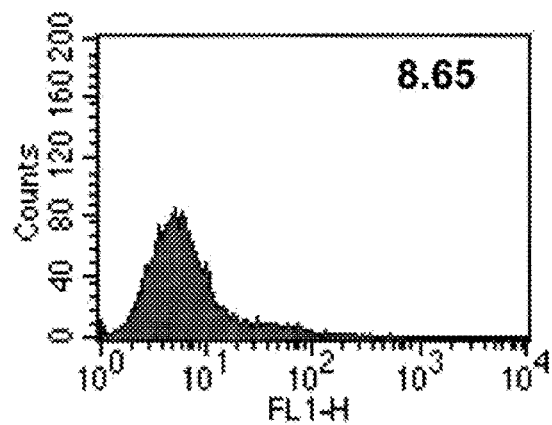
FIGS. 2A-2D, illustrates FACS binding of multifunctional antigen-binding proteins with T6-17, 10 µg of multifunctional antigen-binding proteins containing the bacterial ZZ (FIG. 2B), huZZ (FIG. 2C), or the 1V66 (FIG. 2D) sequence linked to 4D5scFv were incubated with T6-17 cells that express HER2. After wash, cells were then incubated with the FITC-labeled anti-mouse secondary antibody.
Figure 2B:
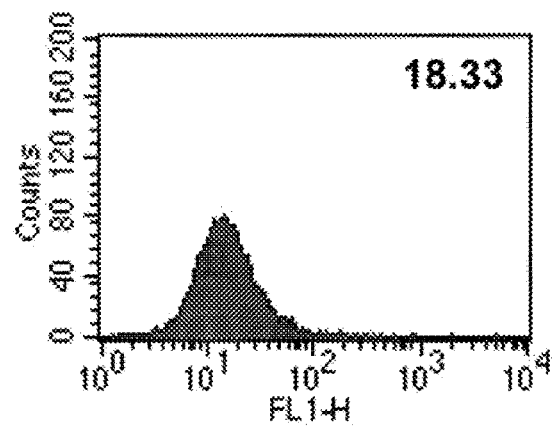
Figure 2C:
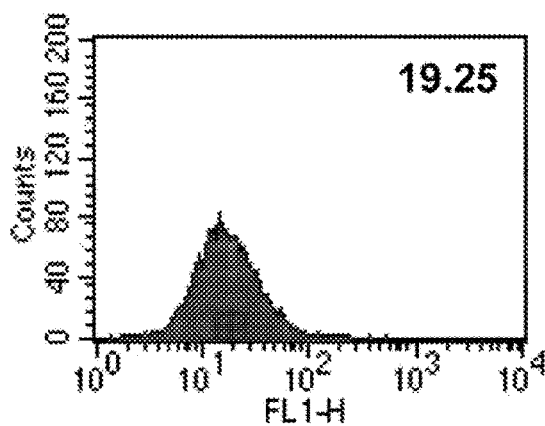
Figure 2D:
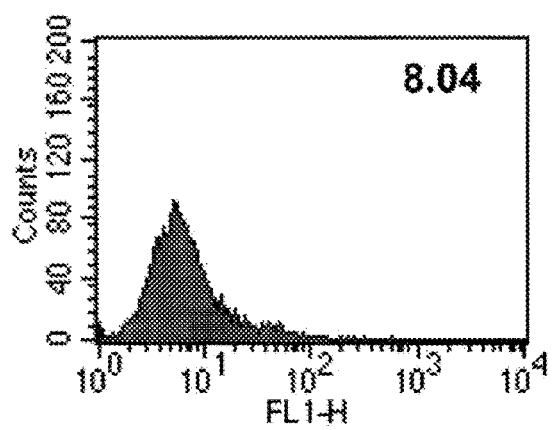
Figure 3A:
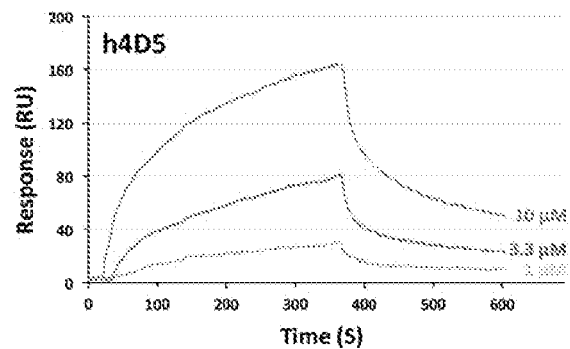
FIGS. 3A-3B, illustrates that huZZ, not the wild type 2FCW sequence, binds to Fc regions of antibodies. Different antibody molecules, h4D5 (top panel), m4D5 (middle panel), and mF77 (lower panel) were immobilized to the chip and allowed to interact with either (FIG. 3A) 4D5scFv-huZZ or (FIG. 3B) 4D5scFv-2FCW (WT) at the indicated concentrations. Interaction of h4D5 and mF77 with h4D5scFv-huZZ was detected.
Figure 3A:
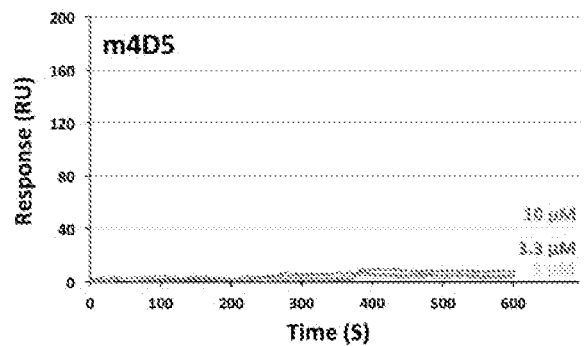
Figure 3A:
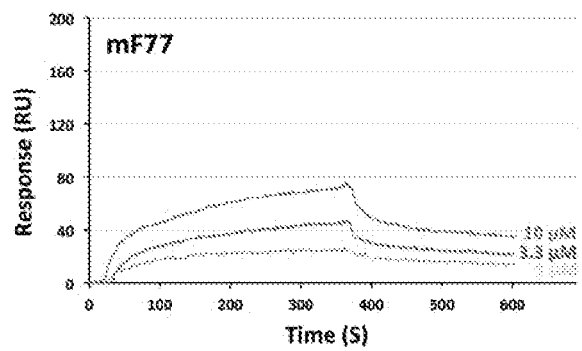
Figure 3B:
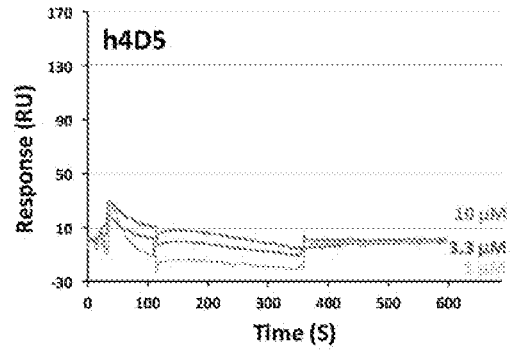
Figure 3B:
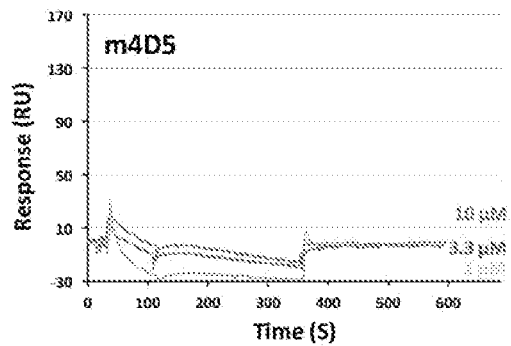
Figure 3B:
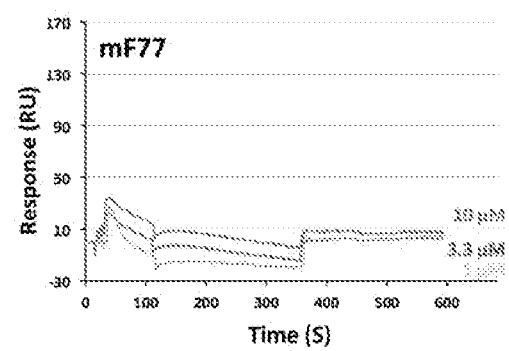

The disclosed compositions and methods may be understood more readily by reference to the following detailed description taken in connection with the accompanying figures, which form a part of this disclosure. It is to be understood that the disclosed compositions and methods are not limited to the specific compositions and methods described and/or shown herein, and that the terminology used herein is for the purpose of describing particular embodiments by way of example only and is not intended to be limiting of the claimed compositions and methods.

Unless specifically stated otherwise, any description as to a possible mechanism or mode of action or reason for improvement is meant to be illustrative only, and the disclosed compositions and methods are not to be constrained by the correctness or incorrectness of any such suggested mechanism or mode of action or reason for improvement.

Throughout this text, the descriptions refer to compositions and methods of using said compositions. Where the disclosure describes or claims a feature or embodiment associated with a composition, such a feature or embodiment is equally applicable to the methods of using said composition. Likewise, where the disclosure describes or claims a feature or embodiment associated with a method of using a composition, such a feature or embodiment is equally applicable to the composition.

Reference to a particular numerical value includes at least that particular value, unless the context clearly dictates otherwise. When a range of values is expressed, another embodiment includes from the one particular value and/or to the other particular value. Further, reference to values stated in ranges include each and every value within that range. All ranges are inclusive and combinable.

When values are expressed as approximations, by use of the antecedent "about," it will be understood that the particular value forms another embodiment.

The term "about" when used in reference to numerical ranges, cutoffs, or specific values is used to indicate that the recited values may vary by up to as much as 10% from the listed value. As many of the numerical values used herein are experimentally determined, it should be understood by those skilled in the art that such determinations can, and often times will, vary among different experiments. The values used herein should not be considered unduly limiting by virtue of this inherent variation. Thus, the term "about" is used to encompass variations of ±10% or less, variations of ±5% or less, variations of ±1% or less, variations of ±0.5% or less, or variations of ±0.1% or less from the specified value. It is to be appreciated that certain features of the disclosed compositions and methods which are, for clarity, described herein in the context of separate embodiments, may also be provided in combination in a single embodiment. Conversely, various features of the disclosed compositions and methods that are, for brevity, described in the context of a single embodiment, may also be provided separately or in any subcombination.

As used herein, the singular forms "a," "an," and "the" include the plural.

Various terms relating to aspects of the description are used throughout the specification and claims. Such terms are to be given their ordinary meaning in the art unless otherwise indicated. Other specifically defined terms are to be construed in a manner consistent with the definitions provided herein.

The term "comprising" is intended to include examples encompassed by the terms "consisting essentially of" and "consisting of." The term "consisting essentially of" is intended to include examples encompassed by the term "consisting of."

As used herein, the term "cytotoxic" or "cytostatic" agent refers to an agent that inhibits the biological processes of a cell, or reduces the viability or proliferative potential of a cell. Cytotoxic or cytostatic agents can function in a variety of ways, for example, but not by way of limitation, by inducing DNA damage, inducing cell cycle arrest, inhibiting DNA synthesis, inhibiting transcription, inhibiting translation or protein synthesis, inhibiting cell division, or inducing apoptosis. As used herein, the term "chemotherapeutic agent" refers to cytotoxic, cytostatic, and antineoplastic agents that preferentially kill, inhibit the growth of, or inhibit the metastasis of neoplastic cells or disrupt the cell cycle of rapidly proliferating cells. Chemotherapeutic agents include, but are not limited to, synthetic compounds, natural and recombinant bacterial toxins, natural and recombinant fungal toxins, natural and recombinant plant toxins, fissionable nuclides, and radionuclides. Specific examples of chemotherapeutic agents include, but are not limited to, pokeweed antiviral protein, abrin, ricin and each of their A chains, momordin, saporin, bryodin 1, bouganin, gelonin, Diphtheria toxin, Pseudomonas exotoxin, Shiga toxin, calicheamicin, maytansinoid, lead-212, bismuth-212, astatine-211, iodine-131, scandium-47, rhenium-186, rhenium-188, yttrium-90, iodine-123, iodine-124, iodine-125, bromine-77, indium-111, boron-10, actinide, altretamine, actinomycin D, plicamycin, puromycin, gramicidin D, doxorubicin, colchicine, cytochalasin B, cyclophosphamide, emetine, maytansine, amsacrine, cisplastin, etoposide, etoposide orthoquinone, teniposide, daunorubicin, gemcitabine, doxorubicin, mitoxantraone, bisanthrene, Bleomycin, methotrexate, vindesine, adriamycin, vincristine, vinblastine, BCNU, taxol, tarceva, avastin, mitomycin, 5-fluorouracil, cyclophosphamide and certain cytokines such as TNF-alpha and TNF-beta.

"Polynucleotide," synonymously referred to as "nucleic acid molecule" or "nucleic acids," refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

The terms "percent identical," "sequence identity," and "percent identity" as used herein refers to the percent of amino acids that are the same (i.e. identical) between two or more polypeptides. Sequence identity between two or more polypeptides can be determined by aligning the amino acid sequences of the polypeptides and scoring the number of positions in the aligned polypeptides that contain the same amino acid residue and comparing that to the number of positions in the aligned polypeptides that differ. Polypeptides can differ at a position, for example, by containing a different amino acid (i.e. substitution or mutation) or by lacking an amino acid (i.e. amino acid insertion or amino acid deletion in one or both of the polypeptides). Sequence identity can be calculated by dividing the number of positions that contain the same amino acid residue by the total number of amino acid residues in the polypeptide. Percent identity, for example, can be calculated by dividing the number of positions that contain the same amino acid residue by the total number of amino acid residues in the polypeptide and multiplying by 100.

"Substantially the same" with respect to nucleic acid or amino acid sequences, means at least about 65% identity between two or more sequences. Preferably, the term refers to at least about 70% identity between two or more sequences, more preferably at least about 75% identity, more preferably at least about 80% identity, more preferably at least about 85% identity, more preferably at least about 90% identity, more preferably at least about 91% identity, more preferably at least about 92% identity, more preferably at least about 93% identity, more preferably at least about 94% identity, more preferably at least about 95% identity, more preferably at least about 96% identity, more preferably at least about 97% identity, more preferably at least about 98% identity, and more preferably at least about 99% or greater identity. Such identity can be determined using mBLAST algorithm (Altschul et at. (1990) Proc. Natl. Acad. Sci. USA 87:2264-8; Karlin and Altschul (1993) Proc. Natl, Acad. Sci, USA 90:5873-7).

As used herein "at least 90% identical to" encompasses at least 90% identical, 91% identical, 92% identical, 93% identical, 94% identical, 95% identical, 96% identical, 97% identical, 98% identical, 99% identical, or 100% identical to the reference item (e.g., a biological sequence).

A "vector" is a replicon, such as plasmid, phage, cosmid, or virus in which another nucleic acid segment may be operably inserted so as to bring about the replication or expression of the segment.

The term "operably linked" or "operably inserted" means that the regulatory sequences necessary for expression of the coding sequence are placed in a nucleic acid molecule in the appropriate positions relative to the coding sequence so as to enable expression of the coding sequence. By way of example, a promoter is operably linked with a coding sequence when the promoter is capable of controlling the transcription or expression of that coding sequence. Coding sequences can be operably linked to promoters or regulatory sequences in a sense or antisense orientation. The term "operably linked" is sometimes applied to the arrangement of other transcription control elements (e.g., enhancers) in an expression vector.

A cell has been "transformed" or "transfected" by exogenous or heterologous nucleic acids such as DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell, or "stable cell" is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

"Biomolecules" include proteins, polypeptides, nucleic acids, lipids, monosaccharides, polysaccharides, and all fragments, analogs, homologs, conjugates, and derivatives thereof.

The terms "express" and "produce" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications. The expression/production of an antibody or antigen-binding fragment can be within the cytoplasm of the cell, and/or into the extracellular milieu such as the growth medium of a cell culture.

The terms "treating" or "treatment" refer to any success or indicia of success in the attenuation or amelioration of an injury, pathology or condition, including any objective or subjective parameter such as abatement, remission, diminishing of symptoms or making the injury, pathology, or condition more tolerable to the patient, slowing in the rate of degeneration or decline, making the final point of degeneration less debilitating, improving a subject's physical or mental well-being, or prolonging the length of survival. The treatment or amelioration of symptoms can be based on objective or subjective parameters; including the results of a physical examination, neurological examination, and/or psychiatric evaluations.

"Effective amount" and "therapeutically effective amount" are used interchangeably herein, and refer to an amount of an antibody, antigen-binding fragment, or antibody composition, as described herein, effective to achieve a particular biological or therapeutic result such as, but not limited to, biological or therapeutic results disclosed, described, or exemplified herein. A therapeutically effective amount of the antibody or antigen-binding fragment thereof may vary according to factors such as the disease state, age, sex, and weight of the individual, and the ability of the antibody or antigen-binding fragment thereof to elicit a desired response in the individual. Such results may include, but are not limited to, the treatment of cancer, as determined by any means suitable in the art.

The term "pharmaceutically acceptable" refers to a compound, additive or composition that is not biologically or otherwise undesirable. For example, the additive or composition may be administered to a subject along with the multifunctional antigen-finding protein without causing any undesirable biological effects or interacting in an undesirable manner with any of the other components of the pharmaceutical composition in which it is contained. Whether a compound, additive or composition is "pharmaceutically acceptable" can be dependent upon factors well-known in the medical field, such as the kind of disease, age, body weight, health status, sex, drug sensitivity of a patient, administration route, administration method, administration frequency, duration of treatment, and drug(s) to be mixed or administered simultaneously in combination.

"Pharmaceutically acceptable carrier" refers to a medium that does not interfere with the effectiveness of the biological activity of the active ingredient(s) and is not toxic to the host to which it is administered.

"Antibody" refers to all isotypes of immunoglobulins (IgG, IgA, IgE, IgM, IgD, and IgY) including various monomeric and polymeric forms of each isotype, unless otherwise specified.

"Antibody fragments" comprise a portion of a full length antibody, generally the antigen binding or variable region thereof, such as Fab, Fab', F(ab')$_2$, and Fv fragments; diabodies; linear antibodies; single-chain antibody molecules; and multispecific antibodies formed from antibody fragments. Various techniques have been developed for the production of antibody fragments, including proteolytic digestion of antibodies and recombinant production in host cells; however, other techniques for the production of antibody fragments will be apparent to the skilled practitioner. In some embodiments, the antibody fragment of choice is a single chain Fv fragment (scFv). "Single-chain Fv" or "scFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv and other antibody fragments, see James D. Marks, Antibody Engineering, Chapter 2, Oxford University Press (1995) (Carl K. Borrebaeck, Ed.).

"Scaffold" refers to a recombinant polypeptide structure that can provide a framework to which another protein or polypeptide may be linked, or fused, to allow for increased stability of the protein or peptide or to place the protein or peptide in a more preferred conformation, or form, to mediate a desired biological activity.

The term "subject" as used herein is intended to mean any animal, in particular, mammals. Although inhibition of tumor growth in mice is exemplified herein, any type of mammal can be treated using the disclosed methods. For example, the disclosed methods are applicable in human, mouse, rat, hamster, guinea pig, rabbit, cat, dog, monkey, donkey, cow, horse, pig, and the like. Thus, the methods are applicable to human and nonhuman animals, although preferably used with mice and humans, and most preferably with humans. "Subject" and "patient" are used interchangeably herein.

As used herein, "therapeutically effective amount" refers to an amount of the multifunctional antigen-binding proteins, as described herein, effective to achieve a particular biological or therapeutic result such as, but not limited to, biological or therapeutic results disclosed, described, or exemplified herein. The therapeutically effective amount may vary according to factors such as the disease state, age, sex, and weight of the individual, and the ability of the composition to cause a desired response in a subject. Exemplary indicators of a therapeutically effect amount include, for example, improved well-being of the patient, reduction of a tumor burden, arrested or slowed growth of a cancer, and/or absence of metastasis of cancer cells to other locations in the body.

"Treat," "treatment," and like terms refer to therapeutic treatment, and includes reducing the severity and/or frequency of symptoms, eliminating symptoms and/or the underlying cause of the symptoms, reducing the frequency or likelihood of symptoms and/or their underlying cause, improving or remediating damage caused, directly or indirectly, by diseases that are associated with defects in the Her2/neu receptor such as cancer. Suitable types of cancers amenable to treatment and/or prevention with the disclosed methods and/or uses include, but are not limited to, breast cancer and stomach cancer. As used herein, "defects in the Her2/neu receptor" include any defect that causes abnormal expression and/or function, including, but not limited to, amplification, activating or inactivating mutations, loss of heterozygosity, deletions of all or a portion of the receptor, amino acid insertions, and the like.

Treatment also includes prolonging survival as compared to the expected survival of a subject not receiving treatment.

"Link" in the context of a scaffold or antigen-binding protein means "connected to" either directly or indirectly. Indirect linkage can be mediated by a polypeptide linker such as poly-glycine or a glycine-serine polypeptide, for example, GGGGS (SEQ ID NO:25) or GGGGGS (SEQ ID NO:26). Other such linkers are known in the art and should be considered to be encompassed by this term.

Novel Recombinant Protein Scaffold

Disclosed herein are multifunctional recombinant protein scaffolds that bind to IgG.

The multifunctional recombinant protein scaffold that binds IgG comprises a human polypeptide that contains mutations that enable the polypeptide to mimic the IgG binding domain of protein A. In some embodiments, the multifunctional recombinant protein scaffold that binds to IgG can comprise a portion of an alpha2-macroglobulin receptor-associated protein (referred to herein as "2FCW"), as illustrated in FIG. 1B. For example, the multifunctional recombinant protein scaffold that binds to IgG can be derived from an un-mutated portion of the alpha2-macroglobulin receptor-associated protein that comprises SEQ ID NO:27. Alternatively, the multifunctional recombinant protein scaffold can comprise, consist of, or consist essentially of a polypeptide that is at least 90% identical to the huZZ domain as set forth as SEQ ID NO:28. In some embodiments, the multifunctional recombinant protein scaffold can comprise, consist of, or consist essentially of a polypeptide that is at least 90% identical to the huZZ1 domain as set forth as SEQ ID NO:29.

TABLE 1

| Exemplary huZZ domains | |
|---|---|
| 2FCW<br>(template)<br>SEQ ID<br>NO: 27 | EEPRVIDLWDLAQSANLTDKELEAFREELKHFEAKI<br>QGDGYTVKKHLQDLSGRISRARH |
| huZZ<br>SEQ ID<br>NO: 28 | Xaa$_1$EPRVXaa$_2$Xaa$_3$LXaa$_4$Xaa$_5$LAXaa$_6$Xaa$_7$AN<br>LTDKEXaa$_8$Xaa$_9$AFXaa$_{10}$Xaa$_{11}$ELKHFXaa$_{12}$AK<br>IQXaa$_{13}$GDGYTVKKHLQDLSGRISRARH<br>wherein Xaa$_1$ is F, L, I, V, or Y;<br>Xaa$_2$ is Q;<br>Xaa$_3$ is N, Q, K, or R;<br>Xaa$_4$ is F or Y;<br>Xaa$_5$ is Y, W, S, or V;<br>Xaa$_6$ is L, F, V, Y, or H;<br>Xaa$_7$ is H, R, D, N, or K;<br>Xaa$_8$ is R, H, Q, or K;<br>Xaa$_9$ is N, Q, S, E, or D,<br>Xaa$_{10}$ is I or L;<br>Xaa$_{11}$ is Q, S, E, A, or K;<br>Xas$_{12}$ is S, V, L, G, or D; and<br>Xaa$_{13}$ is K or no amino acid |
| huZZ1<br>SEQ ID<br>NO: 29 | FEPRVQNLFYLALHANLTDKERNAFIQFLKHFSAKI<br>QGDGYTVKKHLQDLSGRISRARH |

In some embodiments, the multifunctional recombinant protein scaffold can comprise, consist of, or consist essentially of a polypeptide that is at least 90% identical to huZZ as set forth in SEQ ID NO:28. In some embodiments, the multifunctional recombinant protein scaffold can comprise, consist of, or consist essentially of a polypeptide that is at least 90% identical to huZZ1 as set forth in SEQ ID NO:29.

The multifunctional recombinant protein scaffold that binds IgG can comprise a humanized protein A IgG binding domain.

One aspect of the described recombinant scaffold proteins is the ability to provide a framework that will allow one or more antigen-specific binding domains (i.e. antigen-specific peptide or antigen-specific antibody or fragment thereof) to assume a conformation that will cause the peptide to bind an antigen. One desirable aspect of an antigen-binding protein is that it multimerize. Multimeric units will likely have more functional antigen-binding sites available, which can increase the avidity and overall propensity of the antigen-binding protein to bind to its antigen.

Also provided herein are polypeptides comprising the sequence as set forth in SEQ ID NO:28 or SEQ ID NO:29.

Polynucleotides encoding the multifunctional recombinant protein scaffolds are also provided. In some embodiments, the polynucleotide encodes huZZ having an amino acid sequence as set forth in SEQ ID NO:28. In some embodiments, the polynucleotide encodes huZZ1 having an amino acid sequence as set forth in SEQ ID NO:29.

Multifunctional Antigen-Binding Protein

Disclosed herein are multifunctional antigen-binding proteins comprising, at least one multifunctional recombinant protein scaffold that binds to IgG and at least one antigen-specific binding domain,
  wherein the at least one multifunctional recombinant protein scaffold that binds to IgG comprises a human polypeptide that contains mutations that enable the peptide to mimic the IgG binding domain of protein A; and
  wherein the at least one antigen-specific binding domain comprises an antigen-specific peptide, an antigen-specific antibody or fragment thereof, or a combination thereof.

The at least one multifunctional recombinant protein scaffold that binds IgG comprises a human polypeptide that contains mutations that enable the polypeptide to mimic the IgG binding domain of protein A. In some embodiments, the at least one multifunctional recombinant protein scaffold that binds to IgG can comprise a portion of an alpha2-macroglobulin receptor-associated protein. For example, the at least one multifunctional recombinant protein scaffold that binds to IgG can be derived from an un-mutated portion of the alpha2-macroglobulin receptor-associated protein that comprises SEQ ID NO:27. Alternatively, the at least one multifunctional recombinant protein scaffold can comprise, consist of, or consist essentially of a polypeptide that is at least 90% identical to one of the disclosed huZZ domains. In some embodiments, the at least one multifunctional recombinant protein scaffold can comprise, consist of, or consist essentially of a polypeptide that is at least 90% identical to huZZ as set forth in SEQ ID NO:28. In some aspects, for example, the at least one multifunctional recombinant protein scaffold is huZZ as set forth in SEQ ID NO:28. In some embodiments, the at least one multifunctional recombinant protein scaffold can comprise, consist of, or consist essentially of a polypeptide that is at least 90% identical to huZZ1 as set forth in SEQ ID NO:29. In some aspects, for example, the at least one multifunctional recombinant protein scaffold is huZZ1 as set forth in SEQ ID NO:29.

The multifunctional recombinant protein scaffold that binds IgG can comprise a humanized protein A IgG binding domain. Accordingly, provided herein are multifunctional antigen-binding proteins comprising, at least one multifunctional recombinant protein scaffold that binds to IgG and at least one antigen-specific binding domain, wherein the at least one multifunctional recombinant protein scaffold that binds to IgG comprises a humanized protein A IgG binding domain, and wherein the at least one antigen-specific binding domain comprises an antigen-specific peptide, an antigen-specific antibody or fragment thereof, or a combination thereof.

Preferably, the at least one multifunctional recombinant protein scaffold is linked to the antigen-specific binding domain and is capable of binding to a protein other than an antigen which can be bound by the antigen-specific binding domain. Accordingly, multifunctional antigen-binding proteins can not only serve as scaffolds for one or more antigen-specific binding domains, but can also carry out one or more alternative functions, such as binding to a non-antigenic protein. Multifunctional antigen-binding proteins of this sort have two basic features: 1) the ability to provide a framework that maintains, enhances, or allows the ability of an antigen-specific binding domain to bind to its antigen, and 2) the ability to carry out at least one separate biological function, such as binding to another, non-antigen, protein. For example, a multifunctional antigen-binding protein could have the ability to bind to the Fc portion of an antibody, in addition to providing a structural framework for an antigen-specific binding domain. An multifunctional antigen-binding protein incorporating such a scaffold would have the ability to not only bind the antigen corresponding to the antigen-specific binding domain, but would also have the ability to interact with a receptor on a cell surface.

The at least one antigen-specific binding domain comprises an antigen-specific peptide, an antigen-specific antibody or fragment thereof, or a combination thereof. Suitable antigen-specific peptides include, but are not limited to, the polypeptides set forth in SEQ ID NOs:12-24. In some embodiments, the antigen-specific peptide can comprise, consist of, or consist essentially of a polypeptide that is at least 90% identical to any one of SEQ ID NOs:12-24. In some embodiments, the antigen-specific peptide can comprise, consist of, or consist essentially of the polypeptide of any one of SEQ ID NOs:12-24. Suitable antigen-specific antibodies include, for example, full length antibodies or fragments thereof such as scFv, Fab, and/or Fc. For example, the antigen-specific antibody can be 4D5scFv as set forth in SEQ ID NO:30. Thus, in some embodiments, the antigen-specific antibody can comprise, consist of, or consist essentially of a polypeptide that is at least 90% identical to 4D5scFv as set forth in SEQ ID NO:30. In some embodiments, the antigen-specific antibody can comprise, consist of, or consist essentially of a polypeptide that is 4D5scFv as set forth in SEQ ID NO:30.

Accordingly, disclosed herein are multifunctional antigen-binding proteins comprising, at least one multifunctional recombinant protein scaffold that binds to IgG and at least one antigen-specific binding domain, wherein the at least one multifunctional recombinant protein scaffold comprises, consists of, or consists essentially of a polypeptide that is at least 90% identical to huZZ as set forth in SEQ ID NO:28 and the antigen-specific binding domain is an antigen-specific peptide that comprises, consists of, or consists essentially of a polypeptide that is at least 90% identical to any one of SEQ ID NOs:12-24. In some embodiments, the multifunctional antigen-binding proteins can comprise, at least one multifunctional recombinant protein scaffold that binds to IgG and at least one antigen-specific binding domain, wherein the at least one multifunctional recombinant protein scaffold comprises, consists of, or consists essentially of a polypeptide that is at least 90% identical to huZZ1 as set forth in SEQ ID NO:29 and the antigen-specific binding domain is an antigen-specific peptide that comprises, consists of, or consists essentially of a polypep-tide that is at least 90% identical to any one of SEQ ID NOs:12-24.

Also disclosed herein are multifunctional antigen-binding proteins comprising, at least one multifunctional recombinant protein scaffold that binds to IgG and at least one antigen-specific binding domain, wherein the at least one multifunctional recombinant protein scaffold comprises, consists of, or consists essentially of a polypeptide that is at least 90% identical to huZZ as set forth in SEQ ID NO:28 and the antigen-specific binding domain is an antigen-specific antibody that comprises, consists of, or consists essentially of a polypeptide that is at least 90% identical to 4D5scFv as set forth in SEQ ID NO:30. In some embodiments, the multifunctional antigen-binding protein has an amino acid sequence that is at least 90% identical to 4D5scFv-huZZ as set forth in SEQ ID NO:31. In some aspects, the multifunctional antigen-binding protein has the amino acid sequence set forth as SEQ ID NO:31.

The multifunctional antigen-binding proteins can comprise at least one multifunctional recombinant protein scaffold that binds to IgG and at least one antigen-specific binding domain, wherein the at least one multifunctional recombinant protein scaffold comprises, consists of, or consists essentially of a polypeptide that is at least 90% identical to huZZ1 as set forth in SEQ ID NO:29 and the antigen-specific binding domain is an antigen-specific antibody that comprises, consists of, or consists essentially of a polypeptide that is at least 90% identical to 4D5scFv as set forth in SEQ ID NO:30. In some embodiments, the multifunctional antigen-binding protein has an amino acid sequence that is at least 90% identical to 4D5scFv-huZZ1 as set forth in SEQ ID NO:32. In some aspects, the multifunctional antigen-binding protein has the amino acid sequence set forth as SEQ ID NO:32.

The multifunctional recombinant protein scaffold can be on the N-terminus of the antigen-specific binding domain, the C-terminus of the antigen-specific binding domain, or embedded within the antigen-specific binding domain. For example, the disclosed huZZ domains can be linked to a scFV or Fab region or embedded within a Fc region. Although exemplary multifunctional antigen-binding proteins are provided having the protein scaffold on the C-terminus of the antigen-specific binding domain, such exemplary constructs are not meant to be limiting.

The multifunctional antigen-binding proteins can further comprise an interferon (IFN) or a portion thereof attached to the multifunctional recombinant protein scaffold, antigen-specific binding domain, or both. Suitable IFNs include, but are not limited to, human IFN (hIFN) and mouse IFN (mIFN). In some embodiments, for example, the multifunctional antigen-binding protein can comprise, consist of, or consist essentially of, 4D5scFv-huZZ-hIFN as set forth in SEQ ID NO:33. In some embodiments, for example, the multifunctional antigen-binding protein can comprise, consist of, or consist essentially of, an amino acid sequence that is at least 90% identical to 4D5scFv-huZZ-mIFN as set forth in SEQ ID NO:34. In some embodiments, for example, the multifunctional antigen-binding protein can comprise, consist of, or consist essentially of, an amino acid sequence that is at least 90% identical to 4D5scFv -huZZ1-hIFN as set forth in SEQ ID NO:35. In some embodiments, for example, the multifunctional antigen-binding protein can comprise, consist of, or consist essentially of, an amino acid sequence that is at least 90% identical to 4D5scFv-huZZ1-mIFN as set forth in SEQ ID NO:36.

The multifunctional antigen-binding proteins can be labeled or otherwise conjugated to various chemical or biomolecule moieties, for example, for therapeutic or diagnostic applications. The moieties can be cytotoxic, for example, bacterial toxins, viral toxins, radioisotopes, and the like. The moieties can be detectable labels, for example, fluorescent labels, radiolabels, biotin, protein tags and the like, for example a poly-histidine tag. Thus, in some embodiments, the multifunctional antigen-binding protein can further comprise an epitope tag, a fluorophore, a radio isotope, an enzyme, or any combination thereof. In some aspects, the epitope tag is a poly-histidine tag. Suitable poly-histidine tags include, but are not limited to, 6×His-tag.

In addition, solublizing factors can be appended or linked to the multifunctional antigen-binding proteins. Thus, in some embodiments, the multifunctional antigen-binding protein can further comprise a protein domain that promotes solubility. Suitable solubilizing factors include, for example, thioredoxin (Trx) (SEQ ID NO:37).

The multifunctional recombinant protein scaffold and antigen-specific binding domain can be linked either directly or indirectly. For example, a recombinant protein scaffold can be indirectly linked to an antigen-specific binding domain via a polypeptide linker, such as polyglycine or glycine-serine linker. In some embodiments, the multifunctional antigen-binding protein can further comprise a linker having one or more glycine residues, wherein said linker connects the at least one multifunctional recombinant protein scaffold to the at least one antigen-specific binding domain. Suitable linkers include, for example, a linker comprising a polypeptide that is at least 90% identical to SEQ ID NO:25 or SEQ ID NO:26. In some embodiments, the linker can consist of an amino acid sequence of SEQ ID NO:25 or SEQ ID NO:26. In some embodiments a linker can consist essentially of SEQ ID NO:25 or SEQ ID NO:26. Other linkers are well known in the art and are considered within the scope of the subject matter provided herein. (See, for example, Robinson and Sauer, 95 PNAS 5929-34 (1998), Tang et al., 271(26) J. Bio. Chem. 15682-86 (1996)). In addition, the various components of the antigen-binding proteins described herein can be directly linked to one another by splicing together their respective gene segments via genetic engineering techniques well known in the art.

The multifunctional antigen-binding proteins can further comprise one or more additional multifunctional recombinant protein scaffolds as disclosed herein. For example, the one or more additional multifunctional protein scaffolds can comprise, consist of, or consist essentially of a protein segment designed to mimic the CH2 domain of an immunoglobulin heavy chain. One embodiment of this sort of scaffold is exemplified by an amino acid sequence of, or substantially similar to, SEQ ID NO:2. In other embodiments, the one or more additional multifunctional protein scaffolds can comprise, consist of, or consist essentially of, a portion of Protein A. One example of this type of scaffold is embodied by an amino acid sequence of, or substantially similar to, SEQ ID NO:3. Moreover, the one or more additional multifunctional protein scaffolds can comprise, consist of, or consist essentially of a portion of the GITRL protein. In addition to binding antigen, an antigen-binding protein having a GITRL segment would have the ability to interact with cells, such as T cells, that display the receptor for GITRL. One example of such a scaffold is embodied by an amino acid sequence of, or substantially similar to, SEQ ID NO:4.

Multifunctional antigen-binding proteins can take a variety of forms. For example, a multifunctional recombinant protein scaffold can be linked or combined with one or more antigen-specific binding domains to form a multifunctional antigen-binding protein with the ability to bind to an antigen and a cellular protein. In addition, a multifunctional antigen-binding protein can be produced by combining two or more multifunctional recombinant protein scaffolds, where an antigen-specific binding domain is linked to at least one of the multifunctional recombinant protein scaffolds. Furthermore, a multifunctional antigen-binding protein can be produced by combining two or more multifunctional recombinant protein scaffolds, each of which is linked to the same antigen-specific binding domain. Additionally, a multifunctional antigen-binding protein can be produced by combining two or more multifunctional recombinant protein scaffolds, each of which is linked to a different antigen-specific binding domain. As will be apparent to those of skill in the art, numerous possible combinations exist by which one could produce a multifunctional antigen-binding protein using one or more multifunctional recombinant protein scaffolds and one or more antigen-specific binding domains, and while each possibility is not expressly described herein, for the sake of brevity, such scaffold combinations and antigen-specific binding domain are considered to fall within the scope of this disclosure.

Multifunctional antigen-binding proteins could be generated from a multifunctional recombinant protein scaffold having a polypeptide that is at least 90% identical to huZZ as set forth in SEQ ID NO:28 and one or more multifunctional recombinant protein scaffolds exemplified by the amino acid sequences of SEQ ID NO:2, SEQ ID NO:3, or SEQ ID NO:4. In some embodiments, the multifunctional antigen-binding proteins could be generated from a multifunctional recombinant protein scaffold having a polypeptide that is at least 90% identical to huZZ1 as set forth in SEQ ID NO:29 and one or more multifunctional recombinant protein scaffolds exemplified by the amino acid sequences of SEQ ID NO:2, SEQ ID NO:3, or SEQ ID NO:4. In addition, the described multifunctional antigen-binding proteins can incorporate any number of antigen-specific binding domains peptides, such as the antigen-specific peptides of SEQ ID NOs:12-24 and the antigen-specific antibody of SEQ ID NO:30. Multifunctional antigen-binding proteins can be generated by linking a polypeptide that is at least 90% identical to any of huZZ as set faith in SEQ ID NO:28 to a protein designed to mimic a portion of the CH2 domain of an immunoglobulin heavy chain as set forth in SEQ ID NO:2, with an antigen-specific binding domain. For example, a polypeptide that is at least 90% identical to huZZ as set forth in SEQ ID NO:28 can be limited to the AHNP-CH2 mimic as set forth in SEQ ID NO:6. In other aspects, a polypeptide that is at least 90% identical to huZZ1 as set forth in SEQ ID NO:29 can be limited to the AHNP-CH2 mimic as set forth in SEQ ID NO:6. Another embodiment of a multifunctional antigen-binding protein can be generated by linking a polypeptide that is at least 90% identical to huZZ as set forth in SEQ ID NO:28 to a portion of the Protein A ZZ domain as set forth in SEQ ID NO:3, with an antigen-specific binding domain. The antigen-specific binding domain can be an antigen-specific peptide such as AHNP as set forth in SEQ ID NO:12. For example, a polypeptide that is at least 90% identical to huZZ as set faith in SEQ ID NO:28 can be linked to AZZ as set forth in SEQ ID NO:7. In other aspects, a polypeptide that is at least 90% identical to huZZ1 as set forth in SEQ ID NO:29 can be linked to AZZ as set forth in SEQ ID NO:7. The antigen-specific binding domain can be an antigen-specific antibody or portion thereof, such as 4D5scFv. For example, a polypeptide that is at least 90% identical to huZZ as set forth in SEQ ID NO:28 can be linked to 4D5scFv-ZZ as set forth in SEQ ID NO:10. In some aspects, a polypeptide that is at least 90% identical to huZZ1 as set faith in SEQ ID NO:29 can be linked to 4D5scFv-ZZ as set forth in SEQ ID NO:10. Multifunctional antigen-binding proteins can be produced by combining a polypeptide that is at least 90% identical to huZZ as set forth in SEQ ID NO:28 with a ZZ scaffold as set forth in SEQ ID NO:3 which is linked to an existing antigen-binding protein, such as ALZ as set forth in SEQ ID NO:5. For example, a polypeptide that is at least 90% identical to huZZ as set forth in SEQ ID NO:28 can be linked to ALZ-ZZ as set forth in SEQ ID NO:9. In other aspects, a polypeptide that is at least 90% identical to huZZ1 as set forth in SEQ ID NO:29 can be linked to ALZ-ZZ as set forth in SEQ ID NO:9. Multifunctional antigen-binding proteins can be generated by linking a polypeptide that is at least 90% identical to huZZ as set forth in SEQ ID NO:28 to a portion of the GITRL protein as set forth in SEQ ID NO:4, with an antigen-specific binding domain. The antigen-specific binding domain can be an antigen-specific peptide such as AHNP as set forth in SEQ ID NO:12. For example, a polypeptide that is at least 90% identical to huZZ as set forth in SEQ ID NO:28 can be linked to AGITRL as set forth in SEQ ID NO:8. In some aspects, a polypeptide that is at least 90% identical to huZZ1 as set forth in SEQ ID NO:29 can be linked to AGITRL as set forth in SEQ ID NO:8. The antigen-specific binding domain can be an antigen-specific antibody or portion thereof, such as 4D5scFv. For example, a polypeptide that is at least 90% identical to huZZ as set forth in SEQ ID NO:28 can be linked to 4D5scFv-GITRL as set forth in SEQ ID NO:11. In other aspects, a polypeptide that is at least 90% identical to huZZ1 as set forth in SEQ ID NO:29 can be linked to 4D5scFv-GITRL as set forth in SEQ ID NO:11.

In some embodiments, multifunctional antigen-binding proteins can be generated by linking a polypeptide that is at least 90% identical to huZZ as set forth in SEQ ID NO:28, to a recombinant polypeptide derived from a leucine zipper domain (such as a leucine zipper domain derived from the FOX3P protein) as set forth in SEQ ID NO:1, with an antigen-specific binding domain such as AHNP as set forth in SEQ ID NO:12. In some embodiments, multifunctional antigen-binding proteins can be generated by linking a polypeptide that is at least 90% identical to huZZ1 as set forth in SEQ ID NO:29, to a recombinant polypeptide derived from a leucine zipper domain as set forth in SEQ ID NO:1, with an antigen-specific binding domain such as AHNP as set forth in SEQ ID NO:12.

The multifunctional antigen-binding proteins exemplified herein have been made with the antigen-specific peptide AHNP or the antigen-binding antibody 4D5scFv. This practical aspect of the present disclosure should not be considered to limit the disclosed scaffolds to use with only AHNP or 4D5scFv, as it should be apparent that these scaffolds can be used with a wide variety of antigen-specific peptides and scFv proteins or other antibody fragments. Furthermore, while the particular amino acid sequences provided represent the specific embodiments exemplified herein, it should be understood that certain amino acid substitutions, deletions, or additions could be made to the described sequences that would not alter the function of the described scaffolds or antigen-binding proteins.

TABLE 2

Exemplary amino acid sequences of recombinant protein scaffolds and antigen-specific binding domains

| SEQ ID NO. | Protein | Exemplary Amino Acid Sequence |
|---|---|---|
| 1 | LZ domain | MASDFLKHCQADHLLDEKGRAQCLLQREMVQSLE QQLVLEKEKLSAMQAHLAGKMALTKASSVASSDK |
| 2 | CH2 mimic | FPAPLAPGGLYLGG |
| 3 | ZZ domain | VDNKFNKEQQNAFYEILHLPNLNEEQRNAFIQSLKD DPSQSANLLAEAKKLNDAQAPK |
| 4 | GITRL domain | QLETAKEPCMAKFGPLPSKWQMASSEPPCVNKVSD WKLEILQNGLYLIYGQVAPNANYNDVAPFEVRLYK NKDMIQTLTNKSKIQNVGGTYELHVGDTIDLIFNSE HQVLKNNTYWGIILLANPQFIS |
| 5 | ALZ | MAFCDGFYACYMDVGGGGGSMASDFLKHCQADH LLDEKGRAQCLLQREMVQSLEQQLVLEKEKLSAM QAHLAGKMALTKASSVASSDKLEHHHHHH |
| 6 | AHNP-CH2 mimic | MAFCDGFYACYMDVGGGGGSFPAPLAPGGLYLGG ENLYFQGMSDKIIHLTDDSFDTDVLKADGAILVDF WAEWCGPCKMIAPILDEIADEYQGKLTVAKLNIDQ NPGTAPKYGIRGIPTLLLFKNGEVAATKVGALSKGQ LKEFLDANLALEHHHHHH |
| 7 | AZZ | MAFCDGFYACYMDVGGGGGSVDNKFNKEQQNAF YEILHLPNLNEEQRNAFIQSLKDDPSQSANLLAEAK KLNDAQAPKLEHHHHHH |
| 8 | AGITRL | MAFCDGFYACYMDVGGGGGSQLETAKEPCMAKF GPLPSKWQMASSEPPCVNKVSDWKLEILQNGLYLI YGQVAPNANYNDVAPFEVRLYKNKDMIQTLTNKS KIQNVGGTYELHVGDTIDLIFNSEHQVLKNNTYWGI ILLANPQFISLEHHHHHH |
| 9 | ALZ-ZZ | MAFCDGFYACYMDVGGGGGSMASDFLKHCQADH LLDEKGRAQCLLQREMVQSLEQQLVLEKEKLSAM QAHLAGKMALTKASSVASSDKGGGGSELVDNKFN KEQQNAFYEILHLPNLNEEQRNAFIQSLKDDPSQSA NLLAEAKKLNDAQAPKLEHHHHHH |
| 10 | 4D5 scFv-ZZ | MADIQMTQSPSSLSASVGDRVTITCRASQDVNTAV AWYQQKPGKAPKLLIYSASFLYSGVPSRFSGSRSGT DFTLTISSLQPEDFATYYCQQHYTTPPTFGQGTKVE LKRATPSHNSHQVPSAGGPTANSGEVKLVESGGGL VQPGGSLRLSCATSGFNIKDTYIHWVRQAPGKGLE WVARIYPTNGYTRYADSVKGRFTISADTSKNTAYL QMNSLRAEDTAVYYCSRWGGDGFYAMDYWGQGT TVTVSSGGGGSVDNKFNKEQQNAFYEILHLPNLNE EQRNAFIQSLKDDPSQSANLLAEAKKLNDAQAPKL EHHHHHH |
| 11 | 4D5 scFv-GITRL | MADIQMTQSPSSLSASVGDRVTITCRASQDVNTAV AWYQQKPGKAPKLLIYSASFLYSGVPSRFSGSRSGT DFTLTISSLQPEDFATYYCQQHYTTPPTFGQGTKVE LKRATPSHNSHQVPSAGGPTANSGEVKLVESGGGL VQPGGSLRLSCATSGFNIKDTYIHWVRQAPGKGLE WVARIYPTNGYTRYADSVKGRFTISADTSKNTAYL QMNSLRAEDTAVYYCSRWGGDGFYAMDYWGQGT TVTVSSGGGGSQLETAKEPCMAKFGPLPSKWQMAS SEPPCVNKVSDWKLEILQNGLYLIYGQVAPNANYN DVAPFEVRLYKNKDMIQTLTNKSKIQNVGGTYELH VGDTIDLIFNSEHQVLKNNTYWGIILLANPQFISLEH HHHHH |
| 12 | AHNP | FCDGFYACYMDV |
| 13 | AHNPY | YCDGFYACYMDV |
| 14 | B2BPT | YCFPDEEGACY |
| 15 | B2BPT | PCPINCTHSCVDLDDKGCPAEQRASPLTSI |
| 16 | B2APE | YCPIWKFPDEECY |
| 17 | S22 | YCFPDEEGACY |
| 18 | EP1 | YCGYSSTSYCFVMD |
| 19 | EP2 | YCASRDYDYDGRCYFD |
| 20 | EP3 | YCTRGYSSTSYCYAMD |
| 21 | EP4 | FCMEESGGNYCY |
| 22 | EP5 | YCALRGGVYWPCY |
| 23 | EP6 | YCALTYYDYECFAY |
| 24 | B1ALG | YCLVWKYADAGCY |
| 27 | 2FCW | EEPRVIDLWDLAQSANLTDKELEAFREELKHFEAKI QGDGYTVKKHLQDLSGRISRARH |
| 28 | huZZ | Xaa$_1$EPRVXaa$_2$Xaa$_3$LXaa$_4$Xaa$_5$LAXaa$_6$Xaa$_7$ANLTDKEX aa$_8$Xaa$_9$AFXaa$_{10}$Xaa$_{11}$ELKHFXaa$_{12}$AKIQXaa$_{13}$GDGYTV KKHLQDLSGRISRARH |
| 29 | huZZ1 | FEPRVQNLFYLALHANLTDKERNAFIQELKHFSAKI QGDGYTVKKHLQDLSGRISRARH |
| 30 | 4D5scFv | MADIQMTQSPSSLSASVGDRVTITCRASQDVNTAV AWYQQKPGKAPKLLIYSASFLYSGVPSRFSGSRSGT DFTLTISSLQPEDFATYYCQQHYTTPPTFGQGTKVE |

TABLE 2-continued

Exemplary amino acid sequences of recombinant protein scaffolds and antigen-specific binding domains

| SEQ ID NO. | Protein | Exemplary Amino Acid Sequence |
|---|---|---|
| | | LKRATPSHNSHQVPSAGGPTANSGEVKLVESGGGL VQPGGSLRLSCATSGFNIKDTYIHWVRQAPGKGLE WVARIYPTNGYTRYADSVKGRFTISADTSKNTAYL QMNSLRAEDTAVYYCSRWGGDGFYAMDYWGQGT TVTVSS |
| 31 | 4D5scFv-huZZ | *MADIQMPQSPSSLSASVGDRVTITCRASQDVNTAVAWY QQKPGKAPKLLPYSASFLYSGVPSRFSGSRSGTDFTLTIS SLQPEDFATYYCQQHYTTPPTFGQGTKVELKRATPSH NSHQVPSAGGPTANSGEVKLVESGGGLVQPGGSLRLS CATSGFNIKDTYIHWVRQAPGKGLEWVARIYPTNGYTR YADSVKGRFTISADTSKNTAYLQMNSLRAEDTAVYYCSR WGGDGFYAMDYWGQGTTVTVSS*GGGGSVDXaa$_1$EPR VXaa$_2$Xaa$_3$LXaa$_4$Xaa$_5$LAXaa$_6$Xaa$_7$ANLTDKEXaa$_8$Xaa$_9$ AFXaa$_{10}$Xaa$_{11}$ELKHFXaa$_{12}$AKIQXaa$_{13}$GDGYTVKKHL QDLSGRISRARH LEHHHHHH |
| 32 | 4D5scFv-huZZ1 | *MADIQMTQSPSSLSASVGDRVTITCRASQDVNTAVAWY QQKPGKAPKLLIYSASFLYSGVPSRFSGSRSGTDFTLTIS SLQPEDFATYYCQQHYTTPPTFGQGTKVELKRATPSH NSHQVPSAGGPTANSGEVKLVESGGGLVQPGGSLRLS CATSGFNIKDTYIHWVRQAPGKGLEWVARIYPTNGYTR YADSVKGRFTISADTSKNTAYLQMNSLRAEDTAVYYCSR WGGDGFYAMDYWGQGTTVTVSS*GGGGSVDFEPRVQ NLFYLALHANLTDKERNAFIQELKHFSAKIQGDGYT VKKHLQDLSGRISRARHLEHHHHHH |
| 33 | 4D5scFv-huZZ-hIFN | *MADIQMTQSPSSLSASVGDRVTITCRASQDVNTAVAWY QQKPGKAPKLLIYSASFLYSGVPSRFSGSRSGTDFTLTIS SLQPEDFATYYCQQHYTTPPTFGQGTKVELKRATPSH NSHQVPSAGGPTANSGEVKLVESGGGLVQPGGSLRLS CATSGFNIKDTYIHWVRQAPGKGLEWVARIYPTNGYTR YADSVKGRFTISADTSKNTAYLQMNSLRAEDTAVYYCSR WGGDGFYAMDYWGQGTTVTVSS*GGGGSVDXaa$_1$EPR VXaa$_2$Xaa$_3$LXaa$_4$Xaa$_5$LAXaa$_6$Xaa$_7$ANLTDKEXaa$_8$Xaa$_9$ AFXaa$_{10}$Xaa$_{11}$ELKHFXaa$_{12}$AKIQXaa$_{13}$GDGYTVKKHL QDLSGRISRARHLEGGGGSQDPYVKEAENLKKYFN AGHSDVADNGTLFLGILKNWKEESDRKIMQSQIVSF YFKLFKNFKDDQSIQKSVETIKEDMNYKFFNSNKK KRDDFEKLTNYSVTDLNVQRKAIHELIQVMAELSP AAKTGKRKRSQLEHHHHHH |
| 34 | 4D5scFv-huZZ-mIFN | *MADIQMTQSPSSLSASVGDRVTITCRASQDVNTAVAWY QQKPGKAPKLLIYSASFLYSGVPSRFSGSRSGTDFTLTIS SLQPEDFATYYCQQHYTTPPTFGQGTKVELKRATPSH NSHQVPSAGGPTANSGEVKLVESGGGLVQPGGSLRLS CATSGFNIKDTYIHWVRQAPGKGLEWVARIYPTNGYTR YADSVKGRFTISADTSKNTAYLQMNSLRAEDTAVYYCSR WGGDGFYAMDYWGQGTTVTVSS*GGGGSVDXaa$_1$EPR VXaa$_2$Xaa$_3$LXaa$_4$Xaa$_5$LAXaa$_6$Xaa$_7$ANLTDKEXaa$_8$Xaa$_9$ AFXaa$_{10}$Xaa$_{11}$ELKHFXaa$_{12}$AKIQXaa$_{13}$GDGYTVKKHL QDLSGRISRARHLEGGGGSHGTVIESLESLNNYFNS SGIDVEEKSLFLDIWRNWQKDGDMKILQSQIISFYL RLFEVLKDNOAISNNISVIESHLITTFFSNSKAKKDA FMSIAKFEVNNPQVQRQAFNELIRVVHQLLPESSLR KRKRSRLEHHHHHH |
| 35 | 4D5scFv-huZZ1-WFN | *MADIQMTQSPSSLSASVGDRVTITCRASQDVNTAVAWY QQKPGKAPKLLIYSASFLYSGVPSRFSGSRSGTDFTLTIS SLQPEDFATYYCQQHYTTPPTFGQGTKVELKRATPSH NSHQVPSAGGPTANSGEVKLVESGGGLVQPGGSLRLS CATSGFNIKDTYIHWVRQAPGKGLEWVARIYPTNGYTR YADSVKGRFTISADTSKNTAYLQMNSLRAEDTAVYYCSR WGGDGFYAMDYWGQGTTVTVSS*GGGGSVDFEPRNQ NLFYLALHANLTDKERNAFIQELKHFSAKIQGDGYT VKKHLQDLSGRISRARHLEGGGGSQDPYYKEAENL KKYFNAGHSDVADNGTLFLGILKNWKEESDRKIMQ SQIVSFYFKLFKNFKDDQSIQKSVETIKEDMNVKFF NSNKKKRDDFEKLTNYSVTDLNVQRKAIHELIQVM AELSPAAKTGKRKRSQLEHHHHHH |
| 36 | 4D5scFv-huZZ1-mIFN | *MADIQMTQSPSSLSASVGDRVTITCRASQDVNTAVAWY QQKPGKAPKLLIYSASFLYSGVPSRFSGSRSGTDFTLTIS SLQPEDFATYYCQQHYTTPPTFGQGTKVELKRATPSH NSHQVPSAGGPTANSGEVKLVESGGGLVQPGGSLRLS CATSGFNIKDTYIHWVRQAPGKGLEWVARIYPTNGYTR YADSVKGRFTISADTSKNTAYLQMNSLRAEDTAVYYCSR WGGDGFYAMDYWGQGTTVTVSS*GGGGSVDFEPRVQ NLFYLALHANLTDKERNAFIQELKHFSAKIQGDGYT VKKHLQDLSGRISRARHLEGGGGSHGTVIESLESLN NYFSSGIDVEEKSLFLDIWRNWQKDGDMKILQSQI |

TABLE 2-continued

Exemplary amino acid sequences of recombinant protein
scaffolds and antigen-specific binding domains

| SEQ ID NO. | Protein | Exemplary Amino Acid Sequence |
|---|---|---|
| 37 | Thioredoxin (Trx) | <u>ISFYLRLFEVLKDNQAISNNISVIESHLITTFFSNSKA</u><br><u>KKDAFMSIAKFEVNNPQVQRQAFNELIRVVHQLLP</u><br><u>ESSLRKRKRSRL</u>EHHHHHH<br>GAGTMVKQIESKTAFQKALKAAGDKLVVVDFSAT<br>WCGPCKMIKPFFHSLSEKYSNVIFLEVDVDDCQDV<br>ASECEVKCMPTFQFFKKGQKVGEFSGANKKKLEAT<br>INKLV |

For the 4D5scFv-huZZ sequences: 4D5scFv is italicized; an exemplary linker is bold; huZZ and huZZ1 are underlined; IFN is double underlined.

Polynucleotides Encoding Multifunctional Antigen-Binding Proteins

Also disclosed herein are polynucleotides encoding any of the disclosed multifunctional antigen-binding proteins. In some embodiments, the polynucleotide encodes an amino acid sequence at least 90% identical to 4D5scFv-huZZ as set forth in SEQ ID NO:31. In some embodiments, the polynucleotide encodes an amino acid sequence at least 90% identical to 4D5scFv-huZZ1 as set forth in SEQ ID NO:32. In some embodiments, the polynucleotide encodes an amino acid sequence at least 90% identical to 4D5scFv-huZZ-hIFN as set forth in SEQ ID NO:33. In some embodiments, the polynucleotide encodes an amino acid sequence at least 90% identical to 4D5scFv-huZZ-mIFN as set forth in SEQ ID NO:34. In some embodiments, the polynucleotide encodes an amino acid sequence at least 90% identical to 4D5scFv-huZZ1-hIFN as set forth in SEQ ID NO:35. In some embodiments, the polynucleotide encodes an amino acid sequence at least 90% identical to 4D5scFv-huZZ1-mIFN as set forth in SEQ ID NO:36.

The disclosed polynucleotides can also be incorporated into vectors useful for the maintenance, replication, and/or expression of the polynucleotides encoding the described antigen-binding proteins or the described portions thereof. Accordingly, provided herein are vectors comprising: (a) a polynucleotide that encodes an amino acid sequence at least 90% identical to 4D5scFv-huZZ as set forth in SEQ ID NO:31; (b) a polynucleotide that encodes an amino acid sequence at least 90% identical to 4D5scFv-huZZ1 as set forth in SEQ ID NO:32; (c) a polynucleotide that encodes an amino acid sequence at least 90% identical to 4D5scFv-huZZ-hIFN as set forth in SEQ ID NO:33; (d) polynucleotide that encodes an amino acid sequence at least 90% identical to 4D5scFv-huZZ-mIFN as set forth in SEQ ID NO:34; (e) polynucleotide that encodes an amino acid sequence at least 90% identical to 4D5scFv-huZZ1-hIFN as set forth in SEQ ID NO:35; or (f) polynucleotide that encodes an amino acid sequence at least 90% identical to 4D5scFv-huZZ1-mIFN as set forth in SEQ ID NO:36. The vectors described above can be used to engineer cells to express the multifunctional antigen-binding proteins or the described portions thereof encoded by the polynucleotides disclosed herein.

The recombinant protein scaffolds and antigen-specific binding domains described herein can be made by recombinant processes and, therefore, may include amino acid sequences derived from more than one species (i.e., chimeric constructs) or may be engineered to have a human, or human-like, amino acid composition (i.e., a humanized construct). Accordingly, provided herein are vectors comprising polynucleotides capable of encoding the described recombinant protein scaffolds and antigen-specific binding domains. The vectors can be expression vectors. Recombinant expression vectors containing a sequence encoding a polypeptide of interest are thus provided. The expression vector may contain one or more additional sequences such as, but not limited to, regulatory sequences (e.g., promoter, enhancer), a selection marker, and a polyadenylation signal. Vectors for transforming a wide variety of host cells are well known to those of skill in the art. They include, but are not limited to, plasmids, phagemids, cosmids, baculoviruses, bacmids, bacterial artificial chromosomes (BACs), yeast artificial chromosomes (YACs), as well as other bacterial, yeast and viral vectors. The vectors described herein may be integrated into the host genome or maintained independently in the cell or nucleus.

Recombinant expression vectors contemplated to be within the scope of the description include synthetic, genomic, or cDNA-derived nucleic acid fragments that encode at least one recombinant protein which may be operably linked to suitable regulatory elements. Such regulatory elements may include a transcriptional promoter, sequences encoding suitable mRNA ribosomal binding sites, and sequences that control the termination of transcription and translation. Expression vectors, especially mammalian expression vectors, may also include one or more nontranscribed elements such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a host may also be incorporated. Such vectors may be integrated into the host genome or maintained independently in the cell or nucleus.

The vectors described herein can be used to transform various cells with the genes encoding the disclosed recombinant protein scaffolds or antigen-specific binding domains. Accordingly, provided herein are cells genetically engineered to express any of the disclosed polynucleotides or vectors comprising said polynucleotides. For example, provided herein are cells comprising: (a) a polynucleotide that encodes an amino acid sequence at least 90% identical to 4D5scFv-huZZ as set forth in SEQ ID NO:31; (b) a polynucleotide that encodes an amino acid sequence at least 90% identical to 4D5scFv-huZZ1 as set forth in SEQ ID NO:32; (c) a polynucleotide that encodes an amino acid sequence at least 90% identical to 4D5scFv-huZZ-hIFN as set forth in SEQ ID NO:33; (d) polynucleotide that encodes an amino acid sequence at least 90% identical to 4D5scFv-huZZ-mIFN as set forth in SEQ ID NO:34; (e) polynucleotide that encodes an amino acid sequence at least 90% identical to 4D5scFv-huZZ1-hIFN as set forth in SEQ ID NO:35; or (f)

polynucleotide that encodes an amino acid sequence at least 90% identical to 4D5scFv-huZZ1-mIFN as set forth in SEQ ID NO:36.

The vectors may be used to generate recombinant protein scaffold or antigen-specific binding domain-producing cells or cell lines. Thus, another aspect features host cells transformed with vectors comprising a nucleic acid sequence encoding a recombinant protein scaffold or antigen-specific binding domain, such as those disclosed and exemplified herein. The host cells disclosed herein can be prokaryotic or eukaryotic cells. For example the host cell can be a bacteria. In a preferred embodiment, the bacterial host cell is *E. coli*. Of course, the host cell can also be a mammalian cell, such as a Chinese hamster ovary (CHO) cell line. Numerous other such host cells, prokaryotic and eukaryotic, are known in the art and are considered to be within the scope of this disclosure.

Numerous techniques are known in the art for the introduction of foreign genes into cells and may be used to construct the recombinant cells for purposes of carrying out the inventive methods, in accordance with the various embodiments described and exemplified herein. The technique used should provide for the stable transfer of the heterologous gene sequence to the host cell, such that the heterologous gene sequence is heritable and expressible by the cell progeny, and so that the necessary development and physiological functions of the recipient cells are not disrupted. Techniques which may be used include but are not limited to chromosome transfer (e.g., cell fusion, chromosome mediated gene transfer, micro cell mediated gene transfer), physical methods (e.g., transfection, spheroplast fusion, microinjection, electroporation, liposome carrier), viral vector transfer (e.g., recombinant DNA viruses, recombinant RNA viruses) and the like. Calcium phosphate precipitation and polyethylene glycol (PEG)-induced fusion of bacterial protoplasts with mammalian cells can also be used to transform cells.

Methods of Treating Disease in a Subject

Disclosed herein are methods of treating and/or preventing disease in a subject in need thereof comprising, administering to the subject a therapeutically effective amount of a composition comprising one or more of the disclosed multifunctional antigen-binding proteins.

Also disclosed herein are compositions comprising one or more of the disclosed multifunction antigen-binding proteins for use in treating and/or preventing disease in a subject in need thereof.

Also provided is the use of a composition comprising one or more of the disclosed multifunctional antigen-binding proteins in the manufacture of a medicament for the treatment of disease.

In some embodiments, the methods and/or uses comprise administering to the subject a therapeutically effective amount of a composition comprising a multifunctional antigen-binding protein having an amino acid sequence that is at least 90% identical to 4D5scFv-huZZ as set forth in SEQ ID NO:31. In some embodiments, the methods and/or uses comprise administering to the subject a therapeutically effective amount of a composition comprising a multifunctional antigen-binding protein having an amino acid sequence that is at least 90% identical to 4D5scFv-huZZ1 as set forth in SEQ ID NO:32. In some embodiments, the methods and/or uses comprise administering to the subject a therapeutically effective amount of a composition comprising a multifunctional antigen-binding protein having an amino acid sequence that is at least 90% identical to 4D5scFv-huZZ-hIFN as set forth in SEQ ID NO:33. In some embodiments, the methods and/or uses comprise administering to the subject a therapeutically effective amount of a composition comprising a multifunctional antigen-binding protein having an amino acid sequence that is at least 90% identical to 4D5scFv-huZZ-mIFN as set forth in SEQ ID NO:34. In some embodiments, the methods and/or uses comprise administering to the subject a therapeutically effective amount of a composition comprising a multifunctional antigen-binding protein having an amino acid sequence that is at least 90% identical to 4D5scFv-huZZ1-hIFN as set forth in SEQ ID NO:35. In some embodiments, the methods and/or uses comprise administering to the subject a therapeutically effective amount of a composition comprising a multifunctional antigen-binding protein having an amino acid sequence that is at least 90% identical to 4D5scFv-huZZ1-mIFN as set forth in SEQ ID NO:36.

The disclosed methods and/or uses can be used to treat and/or prevent diseases that are associated with defects in the Her2/neu receptor. In some embodiments, the disclosed methods and/or uses can be used to treat cancer. Suitable types of cancers amenable to treatment and/or prevention with the disclosed methods and/or uses include, but are not limited to, breast cancer and stomach cancer. As used herein, "defects in the Her2/neu receptor" include any defect that causes abnormal expression and/or function, including, but not limited to, amplification, activating or inactivating mutations, loss of heterozygosity, deletions of all or a portion of the receptor, amino acid insertions, and the like.

The disclosed multifunctional antigen-binding proteins can be conjugated to one or more chemotherapeutic agents such as, but not limited to radionuclides, toxins, and cytotoxic and cytostatic agents. In other embodiments the multifunctional antigen-binding proteins can be used in combination with one or more chemotherapeutic agents. The multifunctional antigen-binding proteins described herein may be used alone or with (e.g., coadministered or conjugated to) a biomolecule or chemotherapeutic agent such as a cytotoxic or cytostatic agent. In some embodiments, the chemotherapeutic agent can be a radionuclide, including, but not limited to lead-212, bismuth-212, astatine-211, iodine-131, scandium-47, rhenium-186, rhenium-188, yttrium-90, iodine-123, iodine-124, iodine-125, bromine-77, indium-111, and fissionable nuclides such as boron-10 or an actinide. In other embodiments, the chemotherapeutic agent can be a toxin or cytotoxic drug, pokeweed antiviral protein, abrin, ricin and each of their A chains, momordin, saporin, bryodin 1, bouganin, gelonin, Diphtheria toxin, Pseudomonas exotoxin, Shiga toxin, calicheamicin, maytansinoid, altretamine, actinomycin D, plicamycin, puromycin, gramicidin D, doxorubicin, colchicine, cytochalasin B, cyclophosphamide, emetine, maytansine, amsacrine, cisplastin, etoposide, etoposide orthoquinone, teniposide, daunorubicin, gemcitabine, doxorubicin, mitoxantraone, bisanthrene, Bleomycin, methotrexate, pemetrexed, cisplatinum, vindesine, adriamycin, vincristine, vinblastine, BCNU, taxol, tarceva, avastin, mitomycin, 5-fluorouracil, cyclophosphamide, certain cytokines such as TNF-alpha and TNF-beta, and the like. Methods of conjugation of multifunctional antigen-binding proteins to such agents are known in the literature.

In some embodiments, the composition can further comprise a pharmaceutically acceptable carrier. Accordingly, also provided herein are compositions that include one or more of the disclosed multifunctional antigen-binding proteins and a pharmaceutically acceptable carrier.

The compositions can be formulated as any of various preparations that are known and suitable in the art, including those described and exemplified herein. In some embodiments, the compositions can be aqueous formulations. Aqueous solutions can be prepared by admixing the multifunctional antigen-binding proteins in water or suitable physiologic buffer, and optionally adding suitable colorants, flavors, preservatives, stabilizing and thickening agents and the like as desired. Aqueous suspensions can also be made by dispersing the multifunctional antigen-binding proteins in water or physiologic buffer with viscous material, such as natural or synthetic gums, resins, methylcellulose, sodium carboxymethylcellulose, and other well-known suspending agents.

Also included are liquid formulations and solid form preparations which are intended to be converted, shortly before use, to liquid preparations. Such liquids include solutions, suspensions, syrups, slurries, and emulsions. Liquid preparations may be prepared by conventional means with pharmaceutically acceptable additives such as suspending agents (e.g., sorbitol syrup, cellulose derivatives or hydrogenated edible fats or oils); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). These preparations may contain, in addition to the active agent, colorants, flavors, stabilizers, buffers, artificial and natural sweeteners, dispersants, thickeners, solubilizing agents, and the like. The compositions may be in powder or lyophilized form for constitution with a suitable vehicle such as sterile water, physiological buffer, saline solution, or alcohol, before use.

The compositions can be formulated for injection into a subject. For injection, the compositions can be formulated in aqueous solutions such as water or alcohol, or in physiologically compatible buffers such as Hanks's solution, Ringer's solution, or physiological saline buffer. The solution may contain formulatory agents such as suspending, stabilizing and/or dispersing agents. Injection formulations may also be prepared as solid form preparations which are intended to be converted, shortly before use, to liquid form preparations suitable for injection, for example, by constitution with a suitable vehicle, such as sterile water, saline solution, or alcohol, before use.

The compositions can be formulated in sustained release vehicles or depot preparations. Such long acting formulations may be administered by implantation (for example, subcutaneously or intramuscularly) or by intramuscular injection. Thus, for example, the compositions may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well-known examples of delivery vehicles suitable for use as carriers for hydrophobic drugs.

The multifunctional antigen-binding proteins and/or compositions comprising the same may be administered orally in any acceptable dosage form such as capsules, tablets, aqueous suspensions, solutions or the like. The multifunctional antigen-binding proteins may also be administered parenterally including but not limited to: subcutaneous, intravenous, intramuscular, intra-articular, intra-synovial, intrasternal, intranasal, topically, intrathecal, intrahepatic, intralesional, and intracranial injection or infusion techniques. Generally, the multifunctional antigen-binding proteins will be intravenously or intraperitoneally administered, for example, by injection.

The disclosed compositions are useful in the methods and/or uses provided herein for treating or preventing disease in a subject. In one embodiment, the described methods of treatment include administering a therapeutic amount of a one or more of the described multifunctional antigen-binding proteins to a subject in need of such treatment. Similarly, in one embodiment, the described methods of preventing disease in a subject include administering a therapeutic amount of a one or more of the described multifunctional antigen-binding proteins to a subject in need thereof. A preferred method of treating or preventing a disease relate to a disease associated with the Her2/neu receptor or EGFR in a subject, where the treatment or prevention includes administering to the subject a composition including a multifunctional antigen-binding protein described herein.

Subjects can be administered at least one multifunctional antigen-binding protein in a daily dose range of about 0.01 µg to about 500 mg of multifunctional antigen-binding protein per kg of the weight of the subject. The dose administered to the subject can also be measured in terms of total amount of the at least one multifunctional antigen-binding protein administered per day. In some embodiments, a subject is administered about 5 to about 5000 milligrams of at least one multifunctional antigen-binding protein per day. In some embodiments, a subject is administered up to about 10 milligrams of at least one multifunctional antigen-binding protein per day. In some embodiments, a subject is administered up to about 100 milligrams of at least one multifunctional antigen-binding protein per day. In some embodiments, a subject is administered up to about 250 milligrams of at least one multifunctional antigen-binding protein per day. In some embodiments, a subject is administered up to about 500 milligrams of at least one multifunctional antigen-binding protein per day. In some embodiments, a subject is administered up to about 750 milligrams of at least one multifunctional antigen-binding protein per day. In some embodiments, a subject is administered up to about 1000 milligrams of at least one multifunctional antigen-binding protein per day. In some embodiments, a subject is administered up to about 1500 milligrams of at least one multifunctional antigen-binding protein per day, in some embodiments, a subject is administered up to about 2000 milligrams of at least one multifunctional antigen-binding protein per day. In some embodiments, a subject is administered up to about 2500 milligrams of at least one multifunctional antigen-binding protein per day. In some embodiments, a subject is administered up to about 3000 milligrams of at least one multifunctional antigen-binding protein per day. In some embodiments, a subject is administered up to about 3500 milligrams of at least one multifunctional antigen-binding protein per day. In some embodiments, a subject is administered up to about 4000 milligrams of at least one multifunctional antigen-binding protein per day. In some embodiments, a subject is administered up to about 4500 milligrams of at least one multifunctional antigen-binding protein per day. In some embodiments, a subject is administered up to about 5000 milligrams of at least one multifunctional antigen-binding protein per day. In some embodiments, the multifunctional antigen-binding protein is administered to a subject weekly or bi-weekly.

For effective treatment, one skilled in the art may recommend a dosage schedule and dosage amount adequate for the subject being treated. It may be preferred that dosing occur one to four or more times daily for as long as needed. The dosing may occur less frequently if the compositions are formulated in sustained delivery vehicles. The dosage schedule may also vary depending on the active drug concentration, which may depend on the needs of the subject.

Methods of Detecting an Antigen of Interest

Also provided are method of detecting an antigen of interest in a subject comprising, administering any of the disclosed multifunctional antigen-binding protein to the subject and detecting binding of the multifunctional antigen-binding protein to the antigen of interest. Antigens of interest include, but are not limited to, the Her2/neu receptor.

Further provided herein are multifunctional antigen-binding proteins for use in detecting an antigen of interest in a subject, wherein the multifunctional antigen-binding proteins are administered to the subject and binding of the multifunctional antigen-binding protein to the antigen of interest is detected.

In some embodiments, the methods and/or uses comprise administering to the subject a multifunctional antigen-binding protein having an amino acid sequence that is at least 90% identical to 4D5scFv-huZZ as set forth in SEQ ID NO:31 and detecting binding to the Her2/neu receptor. In some embodiments, the methods and/or uses comprise administering to the subject a multifunctional antigen-binding protein having an amino acid sequence that is at least 90% identical to 4D5scFv-huZZ1 as set forth in SEQ ID NO:32 and detecting binding to the Her2/neu receptor.

The disclosed methods and/or uses are applicable to antigen detection in a subject, in a sample obtained from a subject, ex vivo or in vitro.

Suitable detection techniques include, but are not limited to, Western blot, microscopy, ELISA, FACS, detection of radiolabels, and the like.

Methods of Detecting a Disease Associated Protein or Metabolite

Disclosed herein are methods of detecting the Her2/neu receptor comprising, exposing a sample containing the Her2/neu receptor to any of the multifunctional antigen-binding protein disclosed herein and detecting binding of the multifunctional antigen-binding protein to the sample. In some aspects, the detecting is performed in vitro. In some embodiments, the methods comprise exposing a sample containing the Her2/neu receptor to a multifunctional antigen-binding protein having an amino acid sequence that is at least 90% identical to 4D5scFv-huZZ as set forth in SEQ ID NO:31 and detecting binding of the multifunctional antigen-binding protein to the sample. In some embodiments, the methods comprise exposing a sample containing the Her2/neu receptor to a multifunctional antigen-binding protein having an amino acid sequence that is at least 90% identical to 4D5scFv-huZZ1 as set forth in SEQ ID NO:32 and detecting binding of the multifunctional antigen-binding protein to the sample.

In some embodiments, the sample is a biological sample derived from a subject having a disease associated with defects in the Her2/neu receptor. The disclosed methods are applicable to detecting the Her2/neu receptor in a subject, in a sample obtained from a subject, ex vivo or in vitro.

The multifunctional antigen-binding proteins disclosed herein may be used to detect disease-causing agents or disease associated proteins or metabolites in a subject or a sample obtained from a subject, which in turn can allow for a diagnosis. The methods described herein can be particularly applicable to detecting or otherwise assessing the expression of the Her2/neu receptor or EGFR in a subject. For example, one could inject the patient with a detectably labeled embodiment of one of the antigen-binding proteins described herein and detect the localization and/or intensity of the signal in the subject. Alternatively, one could expose a sample containing the Her2/neu receptor or EGFR to the receptor-specific antigen-binding proteins described herein, and detecting binding of said antigen-binding protein to said sample.

Suitable detection techniques include, but are not limited to, Western blot, microscopy, ELISA, FACS, detection of radiolabels, and the like.

The following examples are provided to further describe some of the embodiments described herein with greater detail. They are intended to illustrate, not to limit, the disclosed embodiments.

EXAMPLES

Example 1

Identification of a Human Protein that is Structurally Similar to the IgG Binding Domain of Protein A A class of multifunctional recombinant protein scaffolds which carry an IgG binding-domain of Protein A that interacts with Fc region of immunoglobulins were previously developed (Zhang, 2013). The multifunctional recombinant protein scaffolds can also bind to a target, such as a receptor on the tumor cells, through an antigen-specific binding domain (e.g. an scFv). As a result, the engineered multifunctional antigen-binding protein will direct immune effector cell functions towards tumor cells and have potential therapeutic applications (Cai et al., 2013).

Provided herein is a novel approach to create a human protein to behave like the Z domain and bind to the Fc region of IgG. This humanized Z domain, which is termed huZZ, will replace the Z domain of bacterial origin in multifunctional antigen-binding proteins to reduce the immunogenicity if they are used as therapeutics in human. In addition, the huZZ can be used to replace the Z domain to develop affinity proteins for defined targets using reported phage display or other similar molecular approaches. An example of this will be the "Affibody" that is developed based on the Z domain of bacterial Protein A.

To create the humanized version of the Z domain, the crystal structure of the IgG binding domain of the *Staphylococcus aureus* protein A (PDB code: 1DEE)(Graille et al., 2000) was first used as a model to search for similar structures in Protein Data Bank (http://www.rcsb.org/pdb) using the Dali web server (http://ekhidna.biocenter.helsinki.fi/dali_server) (Holm and Rosenstrom, 2010). From the Dali output list, human proteins were selected and those in which the similar structure parts were not solvent accessible were excluded. Two similar structures were selected: the α2-macroglobulin receptor-associated protein (PDB ID: 2FCW)(Fisher et al., 2006), which had an rmsd of 2.7 angstrom comparing with chain G of 1DEE (FIG. 1A); and SUMO ligase PIAS1 (PDB ID: 1V66)(Okubo et al., 2004), which had an rmsd of 3.1 angstrom. The corresponding fragments were then submitted to the SWISS-MODEL server (Schwede et al., 2003) and structural models were generated.

Based on the model, a short linker (QGD) was created to connect the helixes in 2FCW, A crystal structure (PDB: 1FC2) (Deisenhofer, 1981) revealed the interaction between human IgG Fc and fragment B of protein A. Based on this complex, several mutations were designed in the 2FCW sequence to mimic amino acid residues in the IgG binding domain that contribute to the interaction with Fc, as exemplified in FIG. 1B. The new sequence was named huZZ. A similar design was applied to the PIAS1 sequence and that sequence was named 1V66.

Example 2

Confirmation of huZZ Binding to IgG

The cDNA for huZZ was synthesized and subcloned to generate a multifunctional antigen-binding protein containing an antibody-specific antibody (scFv), 4D5scFvhuZZ. A FACS experiment with the T6-17 cell line was used to verify if huZZ interacts with IgG. T6-17 cells express HER2 and can be recognized by 4D5scFv. When cells were coated with multifunctional antigen-binding proteins containing ZZ (the domain Z from protein A) or huZZ, the FITC-labeled secondary could be captured (FIG. 2). The PIAS1 design was also expressed as 4D5scFv-1V66, but it failed to capture the secondary antibody, indicating that the binding of the FITC-labeled antibody to the cells is dependent on either domain Z or huZZ. In this experiment, the huZZ appeared to have comparable binding activity as domain Z. To further illustrate the binding of huZZ to IgG molecules, a SPR experiment was performed using immobilized IgG species on the chip. As shown in Table 3, 4D5scfv-huZZ demonstrated good binding to m4D5 (human IgG1), mF77 (mouse IgG3) but less well to m4D5 (mouse IgG1). The affinity as determined in the SPR study is somehow lower than that of protein A for IgG. Nevertheless, the binding pattern and preference of huZZ for human IgG1 and mouse IgG3 is similar to that of protein A. As a control, a construct containing the wide type sequence of 2FCW, 4D5scFv-2FCW, was generated. This control construct failed to bind to any antibody molecule significantly, indicating that the mutation introduced into the 2FCW template was critical for the binding of huZZ to Fc fragment.

TABLE 3

Binding affinity ($K_D$, μM) of 4D5scFv-huZZ and 4D5scFv-2FCW (WT) for different IgG molecules as determined by SPR

|  | h4D5 | m4D5 | mF77 |
| --- | --- | --- | --- |
| 4D5scFv-huZZ | 8.4 | weak | 1.4 |
| 4D5scFv-2FCW (WT) | n.d. | n.d. | n.d. |

4D5scFv-huZZ and the control construct 4D5scFv-2FCW were expressed in bacteria, and purified using Nickel-sepharose. It was further concentrated to 10 μM and dialyzed against 0.005% PBST before it was used in Biacore binding experiments, n.d.: not detected.

Example 3

Expression of 4D5scFv-huZZ in 293T Cells

The 4D5scFv-huZZ cDNA was also cloned into a mammalian expression vector and expressed it in 293T cells. Using a similar biacore assay, it was observed that the 293T-expressed 4D5scv-huZZ had better binding affinity for IgG1 (FIG. 4) than the bacterially expressed protein. As shown in FIG. 4A, the 293T protein binds to h4D5 with a $K_D$ of 0.62 μM. The binding to m4D5 was also detectable with a $K_D$ of 1.25 μM. They are all better than what was observed for the bacterially expressed protein (FIG. 3). The affinity for mF77 (IgG3 subtype), however, is about the same.

When 4D5scFv-huZZ was mixed with an Fc fragment of IgG1, a complex was formed in solution. As shown in FIG. 4B, both 4D5scFv-huZZ and Fc were eluted from size exclusion FPLC with a major single peak of molecule weight of 61 and 52 kDa, respectively. The mixture of 4D5scFv-huZZ and Fc showed two peaks of much larger molecular weight. The first peak (fractions #4-7, ~572 kDa) belonged to a large aggregation. The second peak (fractions #9-11) had an estimated molecular weight of 165 kDa. According to the SDS PAGE analysis, the 2 peaks contained both molecules but the 4D5scFv-huZZ contents appeared to be higher than the Fc contents. These data indicate that 4D5scFv-huZZ and Fc form dimer in solution and can form a complex with each other when mixed.

Example 4

In Vitro and In Vivo Activity of huZZ Grababody on Tumor Cells

Next, the activity of two multifunctional antigen-binding proteins containing either the original bacterial domain Z sequence or the humanize sequence huZZ and interferon γ (IFN-γ) were analyzed. In a MTT analysis on the T6-17 cell line, both 4D5scFv-ZZ-mIFN and 4D5scFv-huZZ-mIFN showed dose-dependent activity in the inhibition of proliferation (FIG. 5A) and reached 50% inhibition between 3 and 10 μg/ml for both. 4D5scFv-ZZ-mIFN, which had the original domain Z sequence, had a slightly better activity than 4D5scFv-huZZ-mIFN.

To demonstrate the in vivo activity of huZZ containing multifunctional antigen-binding proteins, the CT26-HER2 implanted tumor model was used. The HER2 tumor line CT-26-HER2 is established in the BALB/c background (Jaime-Ramirez et al., 2011). This is a resistance model for HER2 targeted therapies as tumor cells carry the oncogenic K-Ras$^{G12D}$ mutation (Zhang et al., 2009; Castle et al., 2014). Growth of CT-26-HER2 tumor can be studied in BALB/c mice to understand the effect of host immune cells on HER-2 targeted therapies. Implanted tumors are established by subcutaneous injections of CT-26-HER2 tumor cells ($1 \times 10^6$) in both flank sides of the animal. Treatments of recombinant proteins by i.p. injection, 5 times per week, started the next day after inoculation of tumor cells. As shown in FIG. 5B, both 4D5scFv-ZZ-mIFN and 4D5scFv-huZZ-mIFN were able to inhibit the tumor growth at the dosage of 0.05 mg/kg. The huZZ constructs had a slightly better in vivo activity than the original ZZ construct.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

The disclosures of each patent, patent application, and publication cited or described in this document are hereby incorporated herein by reference, in its entirety.

What is claimed:

1. A multifunctional antigen-binding protein comprising, at least one multifunctional recombinant protein scaffold that binds to IgG and at least one antigen-specific binding domain,
- wherein the at least one multifunctional recombinant protein scaffold that binds to IgG comprises a human polypeptide that contains mutations that enable the polypeptide to mimic the IgG binding domain of protein A,
- wherein the at least one multifunctional recombinant protein scaffold comprises a polypeptide that is:
  - (a) at east 90% identical to huZZ as set forth in SEQ ID NO:28; or
  - (b) at least 90% identical to huZZ1 as set forth in SEQ ID NO:29; and
- wherein the at least one antigen-specific binding domain comprises an antigen-specific peptide, an antigen-specific antibody or fragment thereof, or a combination thereof.

2. The multifunctional antigen-binding protein of claim 1, wherein the at least one multifunctional recombinant protein scaffold that binds to IgG comprises a portion of an alpha2-macroglobulin receptor-associated protein.

3. The multifunctional antigen-binding protein of claim 1, wherein the at least one multifunctional recombinant protein scaffold has the sequence set forth as SEQ ID NO:28 or SEQ ID NO:29.

4. The multifunctional antigen-binding protein of claim 1, wherein the at least one multifunctional recombinant protein scaffold is linked to said antigen-specific binding domain and is capable of binding to a protein other than an antigen which can be hound by the antigen-specific binding domain.

5. The multifunctional antigen-binding protein of claim 1, wherein the antigen-specific peptide comprises a polypeptide that is at least 90% identical to any one of SEQ ID NOs:12-24.

6. The multifunctional antigen-binding protein of claim 1, wherein the antigen-specific antibody comprises a polypeptide that is at least 90% identical to 4D5scFv as set forth in SEQ ID NO:30.

7. The multifunctional antigen-binding protein of claim 6, said multifunctional antigen-binding protein having an amino acid sequence that is:
  - (a) at least 90% identical to 4D5scFv-huZZ as set forth in SEQ NO:31; or
  - (b) at least 90% identical to 4D5scFv-huZZ1 as set forth in SEQ NO:32.

8. The multifunctional antigen-binding protein of claim 1, further comprising a protein domain that promotes solubility.

9. The multifunctional antigen-binding protein of claim 1, further comprising an epitope tag, a fluorophore, a radio isotope, an enzyme, or any combination thereof.

10. The multifunctional antigen-binding protein of claim 9, wherein said epitope tag is a poly-histidine tag.

11. The multifunctional antigen-binding protein of claim 1, further comprising a linker having one or more glycine residues, wherein said linker connects the at least one multifunctional recombinant protein scaffold to the at least one antigen-specific binding domain.

12. The multifunctional antigen-binding protein of claim 11, wherein the linker comprises a polypeptide that is at least 90% identical to SEQ ID NO:25 or SEQ ID NO:26.

13. The multifunctional antigen-binding protein of claim 1, further comprising an interferon (IFN) polypeptide or portion thereof.

14. The multifunctional antigen-binding protein of claim 13, said multifunctional antigen-binding protein having an amino acid sequence that is:
  - (a) at least 90% identical to 4D5scFv-huZZ-hIFN as set forth in SEQ ID NO:33;
  - (b) at least 90% identical to 4D5scFv-huZZ-mIFN as set forth in SEQ ID NO:34;
  - (c) at least 90% identical to 4D5scFv-huZZ1-hIFN as set forth in SEQ ID NO:35; or
  - (d) at least 90% identical to 4D5scFv-huZZ1-mIFN as set forth in SEQ NO:36.

15. A polynucleotide encoding the multifunctional antigen-binding protein of claim 1.

16. A cell that has been genetically engineered to express the polynucleotide of claim 15.

17. A composition comprising the multifunctional antigen-binding protein of claim 1 and a pharmaceutically acceptable carrier.

18. A polypeptide comprising the sequence as set forth in SEQ ID NO:28, SEQ ID NO:29, SEQ ID NO:31, SEQ ID NO:32, SEQ ID NO:33, SEQ NO:34, SEQ ID NO:35, or SEQ ID NO:36.

19. A polynucleotide encoding the polypeptide of claim 18.

* * * * *